(12) United States Patent
Blue et al.

(10) Patent No.: US 9,556,730 B2
(45) Date of Patent: Jan. 31, 2017

(54) FLUID LOSS CONTROL MATERIAL TESTER

(71) Applicant: M-I L.L.C., Houston, TX (US)

(72) Inventors: Aaron Blue, Houston, TX (US); Quanxin Guo, Sugar Land, TX (US)

(73) Assignee: M-I L.L.C., Houston, TX (US)

( * ) Notice: Subject to any disclaimer, the term of this patent is extended or adjusted under 35 U.S.C. 154(b) by 0 days.

(21) Appl. No.: 14/411,508

(22) PCT Filed: Jun. 26, 2013

(86) PCT No.: PCT/US2013/047783
§ 371 (c)(1),
(2) Date: Dec. 28, 2014

(87) PCT Pub. No.: WO2014/004613
PCT Pub. Date: Jan. 3, 2014

(65) Prior Publication Data
US 2015/0143887 A1    May 28, 2015

Related U.S. Application Data

(60) Provisional application No. 61/665,557, filed on Jun. 28, 2012.

(51) Int. Cl.
*E21B 49/08* (2006.01)
*G01N 15/08* (2006.01)
*G01N 33/24* (2006.01)

(52) U.S. Cl.
CPC ............... *E21B 49/08* (2013.01); *G01N 33/24* (2013.01); *G01N 15/088* (2013.01)

(58) Field of Classification Search
USPC ....................................................... 73/152.39
See application file for complete search history.

(56) References Cited

U.S. PATENT DOCUMENTS

| | | | | |
|---|---|---|---|---|
| 4,748,849 | A * | 6/1988 | Jamison | G01N 15/0826 73/53.05 |
| 2008/0236891 | A1 * | 10/2008 | Huynh | G01N 15/08 175/48 |
| 2010/0116494 | A1 | 5/2010 | Fox et al. | |
| 2010/0139914 | A1 * | 6/2010 | Tehrani | G01N 33/241 166/250.17 |
| 2011/0220350 | A1 * | 9/2011 | Daccord | E21B 21/003 166/254.1 |

OTHER PUBLICATIONS

International Search Report and Written Opinion in correspnding PCT Application Serial No. PCT/US2013/047783 dated Oct. 18, 2013, 10 pages.

* cited by examiner

*Primary Examiner* — Lisa Caputo
*Assistant Examiner* — Jamel Williams
(74) *Attorney, Agent, or Firm* — Sara K. M. Hinkley

(57) ABSTRACT

A method for testing a loss control material, the method including filling a testing environment in a testing system with a first fluid, injecting a loss control material in a second fluid into the testing environment from a first end of the testing system, thereby displacing the first fluid across the testing environment to a second end of the testing system, and monitoring a formation of a barrier created by the loss control material.

23 Claims, 11 Drawing Sheets

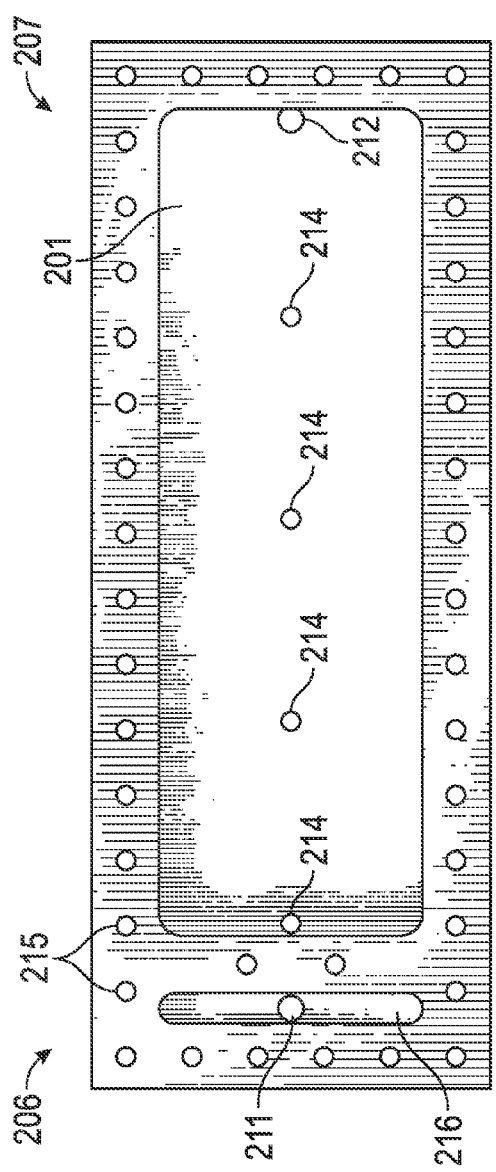
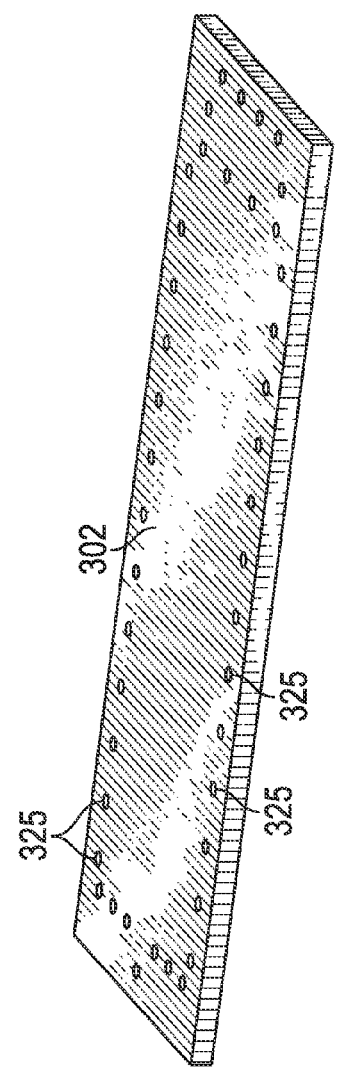
FIG. 2B
FIG. 3

FLUID LOSS CONTROL MATERIAL TESTER

BACKGROUND

During the drilling of a wellbore, various fluids are typically used in the well for a variety of functions. The fluids may be circulated through a drill pipe and drill bit into the wellbore, and then may subsequently flow upward through the wellbore to the surface. During this circulation, the drilling fluid may act to remove drill cuttings from the bottom of the hole to the surface, to suspend cuttings and weighting material when circulation is interrupted, to control subsurface pressures, to maintain the integrity of the wellbore until the well section is cased and cemented, to isolate the fluids from the formation by providing sufficient hydrostatic pressure to prevent the ingress of formation fluids into the wellbore, to cool and lubricate the drill string and bit, and/or to maximize penetration rate.

As stated above, wellbore fluids are circulated downhole to remove rock, as well as deliver agents to combat the variety of issues described above. Fluid compositions may be water-based or oil-based and may comprise weighting agents, surfactants, proppants, and polymers. However, for a wellbore fluid to perform all of its functions and allow wellbore operations to continue, the fluid stays in the borehole. Frequently, undesirable formation conditions are encountered in which substantial amounts or, in some cases, practically all of the wellbore fluid may be lost to the formation. For example, wellbore fluid can leave the borehole through large or small fissures or fractures in the formation or through a highly porous rock matrix surrounding the borehole.

Lost circulation is a recurring drilling problem, characterized by loss of drilling mud into downhole formations. It can occur naturally in formations that are fractured, highly permeable, porous, cavernous, or vugular. These earth formations can include shale, sands, gravel, shell beds, reef deposits, limestone, dolomite, and chalk, among others. The occurrence of a stuck pipe, hole collapse, loss of well control, and loss of or decreased production may be encountered while drilling and producing oil and gas.

Lost circulation may also result from induced pressure during drilling. Specifically, induced mud losses may occur when the mud weight, for well control and to maintain a stable wellbore, exceeds the fracture resistance of the formations. A particularly challenging situation arises in depleted reservoirs, in which the drop in pore pressure weakens hydrocarbon-bearing rocks, but neighboring or inter-bedded low permeability rocks, such as shales, maintain their pore pressure. This can make the drilling of certain depleted zones impossible because the mud weight to support the shale exceeds the fracture resistance of the sands and silts.

Other situations arise in which isolation of certain zones within a formation may be beneficial. For example, one method to increase the production of a well is to perforate the well in a number of different locations, either in the same hydrocarbon bearing zone or in different hydrocarbon bearing zones, and thereby increase the flow of hydrocarbons into the well. Difficulties associated with producing from a well in this manner relates to the control of the flow of fluids from the well and to the management of the reservoir. For example, in a well producing from a number of separate zones (or from laterals in a multilateral well) in which one zone has a higher pressure than another zone, the higher pressure zone may disembogue into the lower pressure zone rather than to the surface. Similarly, in a horizontal well that extends through a single zone, perforations near the "heel" of the well, i.e., nearer the surface, may begin to produce water before those perforations near the "toe" of the well. The production of water near the heel reduces the overall production from the well.

During the drilling process muds are circulated downhole to remove rock as well as deliver agents to combat the variety of issues described above. Mud compositions may be water or oil-based (including mineral oil, biological, diesel, or synthetic oils) and may comprise weighting agents, surfactants, proppants, and gels. In attempting to cure these and other problems, crosslinkable or absorbing polymers, loss control material (LCM) pills, gels, and cement squeezes have been employed.

SUMMARY

According to one aspect, there is provided a method including filling a testing environment in a testing system with a first fluid, injecting a loss control material in a second fluid into the testing environment from a first end of the testing system, thereby displacing the first fluid across the testing environment to a second end of the testing system, and monitoring a formation of a barrier created by the loss control material.

According to another aspect, there is provided a testing system including a first plate having an inlet, an outlet, and a plurality of openings formed through a surface of the first plate, a second plate engaged with the first plate, in which the first plate and the second plate are configured such that a central cavity is formed between a portion of the first plate and the second plate, and a plurality of pressure sensors engaged with the first plate through the plurality of openings formed in the first plate.

This summary is provided to introduce a selection of concepts that are further described below in the detailed description. This summary is not intended to identify key or essential features of the claimed subject matter, nor is it intended to be used as an aid in limiting the scope of the claimed subject matter.

BRIEF DESCRIPTION OF DRAWINGS

FIG. 2B is a top view of the first plate of FIG. 2A.

FIG. 3 is a perspective view of a second plate for receiving a fluid.

DETAILED DESCRIPTION

Figure 1:
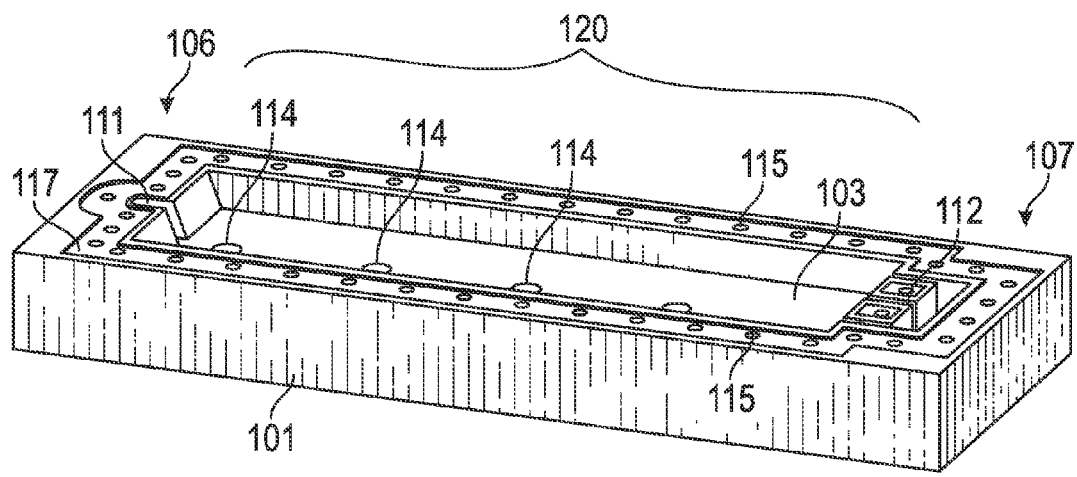
FIG. 1 is a perspective view of a first implementation of a first plate for receiving a fluid.

The following is directed to various exemplary embodiments of the present disclosure. Those having ordinary skill in the art will appreciate that the following description has broad application, and the discussion of any embodiment is meant only to be exemplary of that embodiment, and not intended to suggest that the scope of the disclosure, including the claims, is limited to that embodiment.

Certain terms are used throughout the following description and claims to refer to particular features or components. As those having ordinary skill in the art will appreciate, different persons may refer to the same feature or component by different names. This document does not intend to distinguish between components or features that differ in name but not function. The figures are not necessarily drawn to scale. Certain features and components herein may be shown exaggerated in scale or in somewhat schematic form and some details of conventional elements may not be shown in the interest of clarity and conciseness.

In the following discussion and in the claims, the terms "including" and "comprising" are used in an open-ended fashion, and thus should be interpreted to mean "including, but not limited to . . . ." Also, the term "couple," "coupled to," or "couples" is intended to mean either an indirect or direct connection. Thus, if a first component is coupled to a second component, that connection may be through a direct connection, or through an indirect connection via other components, devices, and connections.

As will be discussed below, one or more aspects are directed to an off-line testing system and associated methods for testing and evaluating loss control materials, in particular, to evaluate the ability of a loss control material to reduce or prevent fluid loss to a formation. In one or more embodiments, a fluid, such as a loss control material, drilling mud material, water, or any combination thereof, for example, may be injected into the testing system, which may simulate the formation. In one or more embodiments, a flow profile of one or more fluids (flowing and/or setting up to form a barrier) may be evaluated visually, through a first plate of the testing system, and/or through a plurality of pressure readings that may be taken by a plurality of pressure sensors engaged along a length of the testing system (simulating a depth into the formation). For example, in one or more embodiments, a user may be able to evaluate the effectiveness of a loss control material, visually and/or by measuring and recording a pressure profile for each fluid at each point along the length of the testing system that includes a pressure sensor.

According to another aspect, there is provided a method for testing a loss control material, the method including filling a testing environment in a testing system (including, but not limited to the testing systems shown in FIGS. 1-7) with a first fluid, injecting a loss control material in a second fluid into the testing environment from a first end of the testing system, thereby displacing the first fluid across the testing environment to a second end of the testing system, and monitoring a formation of a barrier created by the loss control material. In one more embodiments, the method also includes injecting a third fluid into the testing system. In one or more embodiments, each of the first fluid, the second fluid, and the third fluid each may include a drilling mud material and/or water.

In one or more embodiments, monitoring the formation of the barrier created by the loss control material may include collecting data from a plurality of pressure sensors. In one or more embodiments, collecting data from the plurality of pressure sensors may include measuring pressure at the first end of the testing system, the second end of the testing system, and at any point in between the first end and the second end of the testing system.

In one or more embodiments, the method for testing a loss control material may include providing a testing system, the testing system including a first plate having an inlet, an outlet, and a plurality of openings formed through a surface of the first plate, a second plate engaged with the first plate, and a plurality of pressure sensors engaged with the first plate through the plurality of openings formed in the first plate. As discussed herein, in one or more embodiments, a central cavity of the testing system may be formed between a portion of the first plate and the second plate. In one or more embodiments, the inlet of the testing system may be configured to allow a fluid, (e.g., a drilling mud and/or water, and/or a loss control material) to be introduced into the central cavity of the testing system, e.g., the testing environment. Further, the outlet of the testing system may be configured to allow a fluid, as discussed above, and/or a loss control material to exit the central cavity of the testing system.

Referring now to FIG. 1, a perspective view of one implementation of a first plate 101, some aspects of which are in accordance with embodiments disclosed herein, is shown. As shown, the first plate 101 has a central cavity 103 formed therein. As will be discussed below, the central cavity 103 of the first plate 101 may be configured to receive a fluid (not shown) and/or a plurality of spherical testing units (not shown). In one or more embodiments, the first plate 101 may be formed from a pressure-resistant material. In one or more embodiments, the pressure-resistant material of the first plate 101 may allow for at least some transparency. Those having ordinary skill in the art will appreciate that the first plate 101 may be formed from any pressure-resistant material allowing at least some transparency known in the art. For example, in one or more embodiments, the first plate 101 may be formed from a pressure-resistant acrylic which allows for some transparency. Further, in one or more embodiments, the first plate 101 may be formed from polyethylene.

In one or more embodiments, the transparency of the first plate 101 may allow a user to visually inspect and monitor a fluid (not shown) that is disposed within the central cavity 103 of the first plate 101. For example, the transparency of the first plate 101 may allow a user to visually inspect and monitor a profile of a fluid that is disposed within the central cavity 103 of the first plate 101. The fluid, according to embodiments disclosed herein, may include, without limitation, a loss control material, drilling mud material, and/or water. Those having ordinary skill in the art will appreciate that the fluid is not limited to only the above mentioned materials and may include any fluid or material known in the art.

Further, in one or more embodiments, the first plate 101 may include a plurality of openings 114 formed on a surface of the first plate 101. As shown, the plurality of openings 114 are formed on a bottom surface of the first plate 101 at a lower end the central cavity 103. In one or more embodiments, the plurality of openings 114 may be configured to receive a plurality of pressure sensors (not shown). For example, in one or more embodiments, the plurality of pressure sensors may be engaged with the first plate 101 through the plurality of openings 114 formed on a bottom surface of the first plate 101 at a lower end of the central cavity 103.

In one or more embodiments, the pressure sensors may be configured to monitor and collect data regarding a pressure of a fluid (not shown) contained within the central cavity 103 of the first plate 101. Those having ordinary skill in the art will appreciate that the pressure sensors, according to embodiments disclosed herein, may be any type of pressure sensor known in the art. For example, in one or more embodiments, the pressure sensors may be any pressure sensor known in the art that can monitor and collect data regarding a pressure of the fluid contained within the central cavity 103 of the first plate 101.

Further, in one or more embodiments, a data acquisition unit (not shown) may be operatively coupled to the plurality of pressure sensors. In one or more embodiments, the data acquisition unit may be configured to receive, handle, record, store, transfer, and/or process data collected by the plurality of pressure sensors. For example, in one or more embodiments, the data acquisition unit may store and organize pressure data according to different fluids and according to different testing environments. As will be discussed below, the testing environment 120, e.g., the central cavity 103 of the first plate 101, may be altered based on the presence of a plurality of spherical testing units (not shown), as well as by the presence of additional plates (not shown) disposed within the central cavity 103 of the first plate 101, which may alter the volume of the central cavity 103 of the first plate 101.

Although the plurality of openings 114 shown in FIG. 1 may be substantially evenly or equally spaced along a length of the first plate 101, in one or more embodiments, the openings 114 may not necessarily be evenly or equally spaced along a length of the first plate 101. For example, in one or more embodiments, the plurality of openings 114 may be formed in a variable profile along a length of the first plate 101.

For the following example, a first opening 114 may be closer to the first side 106 of the first plate 101 than a second opening 114, and the second opening 114 may be closer to the first side 106 of the first plate 101 than a third opening 114. In one or more embodiments, a distance between a first opening 114 and a second opening 114 may be larger than a distance between the second opening 114 and a third opening 114 of the plurality of openings 114. Alternatively, in one or more embodiments, a distance between two of the openings 114 may be smaller than a distance between two other openings 114.

Further, in one or more embodiments, spacing between openings formed near the first end 106 of the first plate 101 may be larger than spacing between openings formed near the second end 107 of the first plate 101. Alternatively, in one or more embodiments, spacing between openings formed near the first end 106 of the first plate 101 may be smaller than spacing between openings formed near the second end 107 of the first plate 101. In other words, the configuration and spacing of the plurality of openings 114, i.e., the configuration of the pressure sensors, may be distributed according to the interest of the user or tester, which may be any configuration or spacing.

Further, although four openings 114 are shown in FIG. 1, those having ordinary skill in the art will appreciate that, along with the configuration and spacing of the plurality of openings 114, the number of the plurality of openings 114 is not limited to the number of openings 114 shown in FIG. 1. For example, in one or more embodiments, the first plate 101 may have one, two, three, four, five, six, seven or more openings 114 formed in a surface of the first plate 101.

As shown, the first plate 101 has a first end 106 and a second end 107. In one or more embodiments, an inlet 111 may be formed on the first end 106 of the first plate 101. In one or more embodiments, a pump (not shown) may be coupled to the first end 106 of the first plate 101. In one or more embodiments, the pump may be coupled to the inlet 111 formed on the first end 106 of the first plate 101. In one or more embodiments, the pump may be directly coupled to the inlet 111 of the first plate 101. Alternatively, in one or more embodiments, the pump may be coupled to the inlet 111 of the first plate 101 through a pipe or a conduit.

Further, in one or more embodiments, the pump may be configured to pump or inject a fluid into the inlet 111 of the first plate 101. For example, in one or more embodiments, the pump may be configured to inject water or a drilling mud material into the inlet 111 of the first plate. Those having ordinary skill in the art will appreciate that the pump may be any pump or fluid injection device or mechanism known in the art and may be configured to pump or inject any fluid known in the art.

Still referring to FIG. 1, the first plate 101 includes a plurality of engagement openings 115 formed therethrough. As shown, the plurality of engagement openings 115 are formed substantially around an outer edge of the first plate 101. In one or more embodiments, each of the plurality of engagement openings 115 may be configured to receive at least one engagement member (not shown). As will be discussed below, the at least one engagement member may engage the first plate 101 to a second plate (not shown), which may provide a seal over the central cavity 103 of the first plate 101. Further, as will be discussed below, in one or more embodiments, the at least one engagement member may include, without limitation, a threaded rod (not shown), a threaded nut (not shown) configured to engage with the threaded rod, and/or a washer (not shown) that may be disposed between the threaded nut and a surface of one of the first plate 101 and the second plate. Similar to the openings 114 discussed above, the number of engagement openings 115 and the spacing of the engagement openings 115 may vary according to the interest of the user and are not limited to the configuration shown in FIG. 1.

In one or more embodiments, the first plate 101 may include a recessed portion 117 formed on a top surface of the first plate 101. In one or more embodiments, the recessed portion 117 may be formed around a perimeter of the top surface of the first plate 101 and the plurality of engagement openings 115 may be formed in the recessed portion 117. In one or more embodiments, the recessed portion 117 may form a lip, or raised edge, around an outer edge of the first plate 101. As will be discussed below, a second plate (not shown) may be engaged with the first plate 101 and may provide a seal over the central cavity 103 of the first plate 101.

Further, in one or more embodiments, the recessed portion 117 may provide an area for a deformable sealing member (not shown) to be disposed, and deform around the lip of the first plate 101, which may provide a pressure-tight seal around the engagement openings 115 of the first plate 101. Those having ordinary skill in the art will appreciate that the recessed portion 117 may be recessed any distance known in the art into the first plate 101. For example, in one or more embodiments, the recessed portion 117 may be formed 1 mm below a surface, e.g., an upper surface or a lower surface, of the first plate 101. Alternatively, in one or more embodiments, the recessed portion 117 may be formed 2 mm, 3 mm, 4 mm, or more, or any distance in between, below a surface of the first plate 101. Alternatively, in one or more embodiments, the first plate 101 may not necessarily include the recessed portion 117 formed around the plurality of engagement openings 115.

In one or more embodiments, an outlet 112 may be formed on the second end 107 of the first plate 101. In one or more embodiments, an accumulator (not shown) may be coupled to the outlet 112 formed on the second end 107 of the first plate 101. In one or more embodiments, the accumulator may be configured to collect and receive a fluid that is injected into the central cavity 103 of the first plate 101 through the outlet 112. For example, in one or more embodiments, the accumulator may collect and receive a fluid, e.g., loss control material, water, and/or drilling mud material, through the outlet 112 of the first plate 101. In one or more embodiments, the accumulator may also measure a volume change of the fluid within the central cavity 103 of the first plate 101, to keep a pressure within the central cavity 103 of the first plate 101 constant. In one or more embodiments, it may be desirable to maintain a specific pressure within the central cavity 103 of the first plate 101 or within the accumulator. As such, in one or more embodiments, the rate of intake of the accumulator may be automatically adjusted to maintain the desired pressure. In one or more embodiments, it may be desirable to maintain a pressure of between 1 psi and 10 psi within the central cavity 103 of the first plate 101 and/or the accumulator. However, those having ordinary skill in the art will appreciate that the testing system, according to embodiments disclosed herein, may be adapted to maintain a pressure of more than 10 psi within the central cavity 103 of the first plate and/or the accumulator.

Figure 2A:
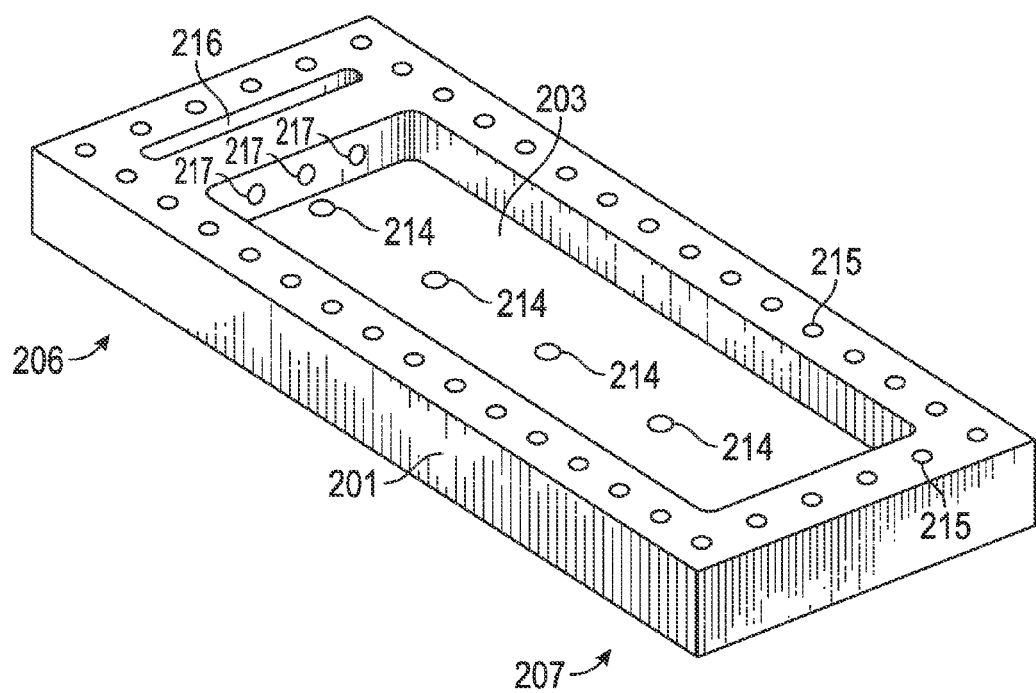
FIG. 2A is a perspective view of a second implementation of a first plate for receiving a fluid.

Referring now to FIGS. 2A and 2B, a perspective view and top view of a second implementation of a first plate 201, according to embodiments described herein, are shown, respectively. As discussed above, in one or more embodiments, the first plate 201 may be formed from a pressure-resistant material that allows at least some transparency. Those having ordinary skill in the art will appreciate that the first plate 201 may be formed from any pressure-resistant material allowing at least some transparency known in the art. For example, in one or more embodiments, the first plate 201 may be formed from a pressure-resistant acrylic which allows some transparency. Further, in one or more embodiments, the first plate 201 may be formed from polyethylene.

As shown, the first plate 201 includes a central cavity 203 formed therein. Those having ordinary skill in the art will appreciate that the central cavity 203 may be formed into the first plate 201 with any distance or at any depth known in the art. For example, in one or more embodiments, the central cavity 203 may be formed 25 mm into a surface, e.g., an upper surface, of the first plate 201. Alternatively, in one or more embodiments, the central cavity 203 may be formed 1 mm, 2 mm, 10 mm, 20 mm, 30 mm, or more, or any distance in between, into a surface of the first plate 201.

Further, as shown, the first plate 201 may include a plurality of openings 214 formed along a length of the first plate 201. As discussed above, in one or more embodiments, the plurality of openings 214 may be configured to receive and engage a plurality of pressure sensors (not shown). In other words, in one or more embodiments, each of the plurality of openings 214 may be configured to engage one of a plurality of pressure sensors.

As discussed above, although the plurality of openings 214 shown in FIGS. 2A and 2B may be substantially evenly or equally spaced along a length of the first plate 201, in one or more embodiments, the openings 214 may not necessarily be evenly or equally spaced along a length of the first plate 201. For example, in one or more embodiments, the plurality of openings 214 may be formed in a variable profile along a length of the first plate 201.

Further, as discussed above, although four openings 214 are shown in FIGS. 2A and 2B, those having ordinary skill in the art will appreciate that, along with the configuration and spacing of the plurality of openings 214, the number of openings in the plurality of openings 214 is not limited to the number of openings 214 shown in FIGS. 2A and 2B. For example, in one or more embodiments, the first plate 201 may have two, three, four, five, six, seven or more openings 214 formed in a surface of the first plate 201.

As shown in FIGS. 2A and 2B, the first plate 201 has a first end 206 and a second end 207. In one or more embodiments, an inlet 211 may be formed within a distribution chamber 216 that may be formed on the first end 206 of the first plate 201. As such, in one or more embodiments, a fluid (not shown) may be introduced through the inlet 211, shown in FIG. 2B, and into the distribution chamber 216.

Further, in one or more embodiments, the distribution chamber 216 may include one or more distribution openings 217. As shown in FIG. 2A, the one or more distribution openings 217 may be formed through a portion of the distribution chamber 216 between the distribution chamber 216 and the central cavity 203. In one or more embodiments, the distribution openings 217 of the distribution chamber 216 may be used to evenly distribute fluid injected from the inlet 211 into the central cavity 203 of the first plate 201. Those having ordinary skill in the art will appreciate that any number of distribution openings 217 may be formed into the distribution chamber 216. For example, in one or more embodiments, the distribution chamber 216 may include one, two, three, four, or more distribution openings 217. Alternatively, in one or more embodiments, the first plate 201 may not necessarily include a distribution chamber 216 or any distribution openings 217.

As discussed above, in one or more embodiments, a pump (not shown) may be coupled to the first end 206 of the first plate 201. In one or more embodiments, the pump may be coupled to the inlet 211 of the first plate 201. For example, in one or more embodiments, the pump may be coupled to the inlet 211 via a tubing (not shown) or a conduit (not shown). Those having ordinary skill in the art will appreciate that the pump may be any pump or fluid injection device or mechanism known in the art and may be configured to pump or inject any fluid known in the art.

Further, as discussed above, in one or more embodiments, an accumulator (not shown) may be coupled to the second end 207 of the first plate 201. In one or more embodiments, the accumulator may be coupled to an outlet 212 formed on the second end 207 of the first plate 201. In one or more embodiments, the accumulator may be configured to collect and receive a fluid that is injected into the central cavity 203 of the first plate 201 through the outlet 212.

Further, as shown, the first plate 201 includes a plurality of engagement openings 215 formed therethrough. As shown, the plurality of engagement openings 215 may be formed substantially around an outer edge of the first plate 201. In one or more embodiments, each of the plurality of engagement openings 215 may be configured to receive at least one engagement member (not shown). As will be discussed below, the at least one engagement member may engage the first plate 201 to a second plate (not shown), which may provide a seal over the central cavity 203 of the first plate 201. Further, as will be discussed below, in one or more embodiments, the at least one engagement member may include, with limitation, a threaded rod (not shown), a threaded nut (not shown) configured to engage with the threaded rod, and a washer (not shown) that may be disposed between the threaded nut and a surface of one of the first plate 201 and the second plate.

Moving to FIG. 3, a perspective view of a first implementation of a second plate 302, according to embodiments disclosed herein, is shown. In one or more embodiments, the second plate 302 may be formed from aluminum. However, those having ordinary skill in the art will appreciate that the second plate 302 may be formed from any substantially rigid material known in the art. For example, in one or more embodiments, the second plate 302 may be formed from acrylic, steel, or any other metal known in the art.

As shown, the second plate 302 includes a plurality of engagement openings 325 formed therethrough. As shown, the engagement openings 325 are formed substantially around an outer edge of the second plate 301. Similar to the plurality of engagement openings 115 and 215 of the first plate shown in FIGS. 1, 2A, and 2B, in one or more embodiments, each of the plurality of engagement openings 325 may be configured to receive at least one engagement member (not shown). Similar to the plurality of openings 114 discussed above in FIG. 1, the number of engagement openings 325 and the spacing of the engagement openings 325 may vary according to the interest of the user and are not limited to the configuration shown in FIG. 3.

In one or more embodiments, the plurality of engagement openings 325 defined by the second plate 302 may be configured to substantially match the configuration of the plurality of engagement holes (not shown) formed in a first plate (not shown), e.g., the engagement holes 115 of the first plate 101 shown in FIG. 1, or the engagement holes 215 of the first plate 201 shown in FIGS. 2A and 2B. In one or more embodiments, the engagement holes of the first plate and the engagement holes 325 of the second plate 301 may be substantially aligned such that the at least one engagement member may disposed through each of the plurality of engagement holes 325 of the second plate and through each of the plurality of engagement holes of a first plate. As such, in one or more embodiments, the at least one engagement member may be used to engage the first plate with the second plate 302.

Figure 4A:
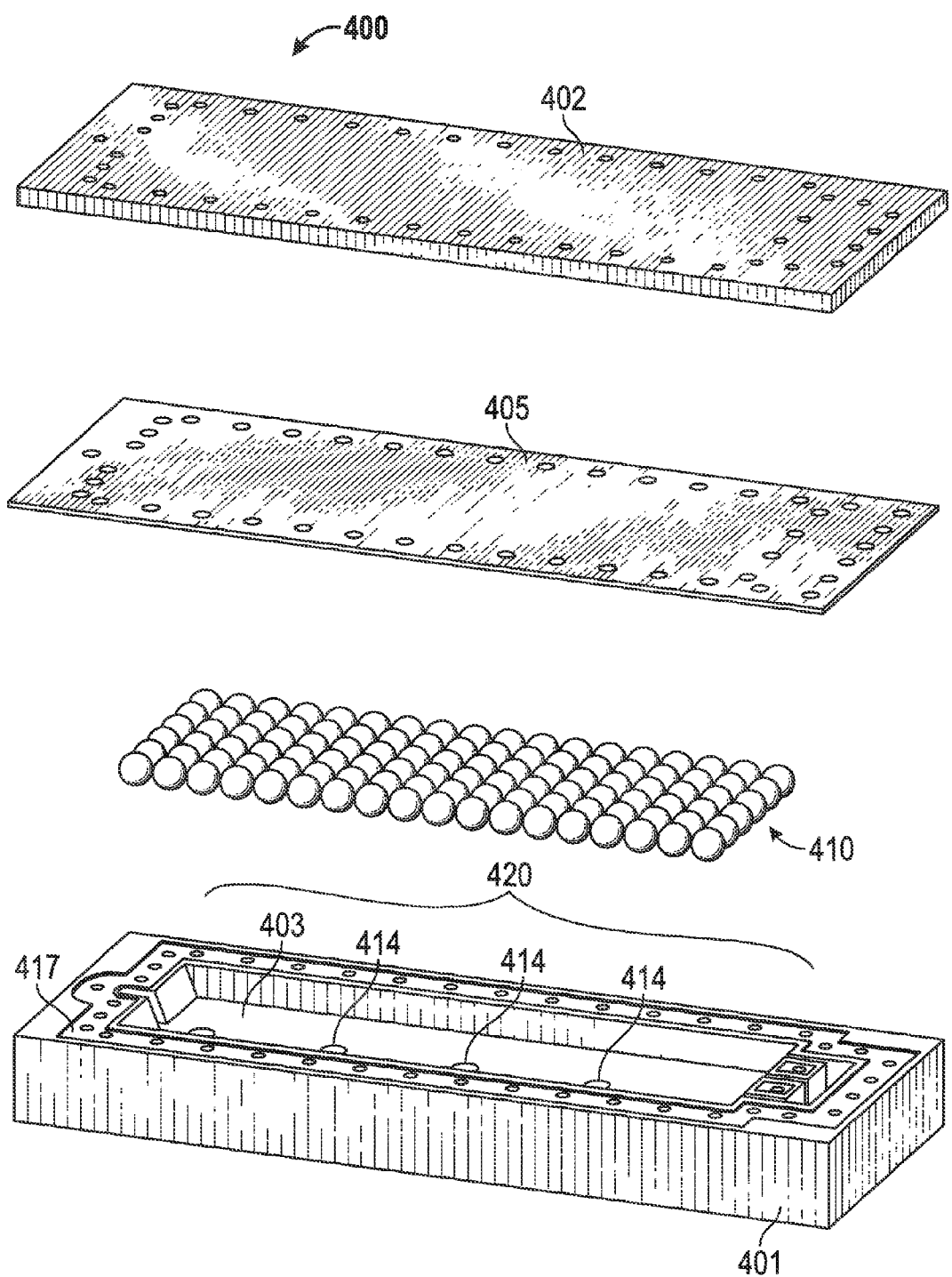
FIGS. 4A-4B are exploded views of a first implementation of a testing system.
Figure 4B:
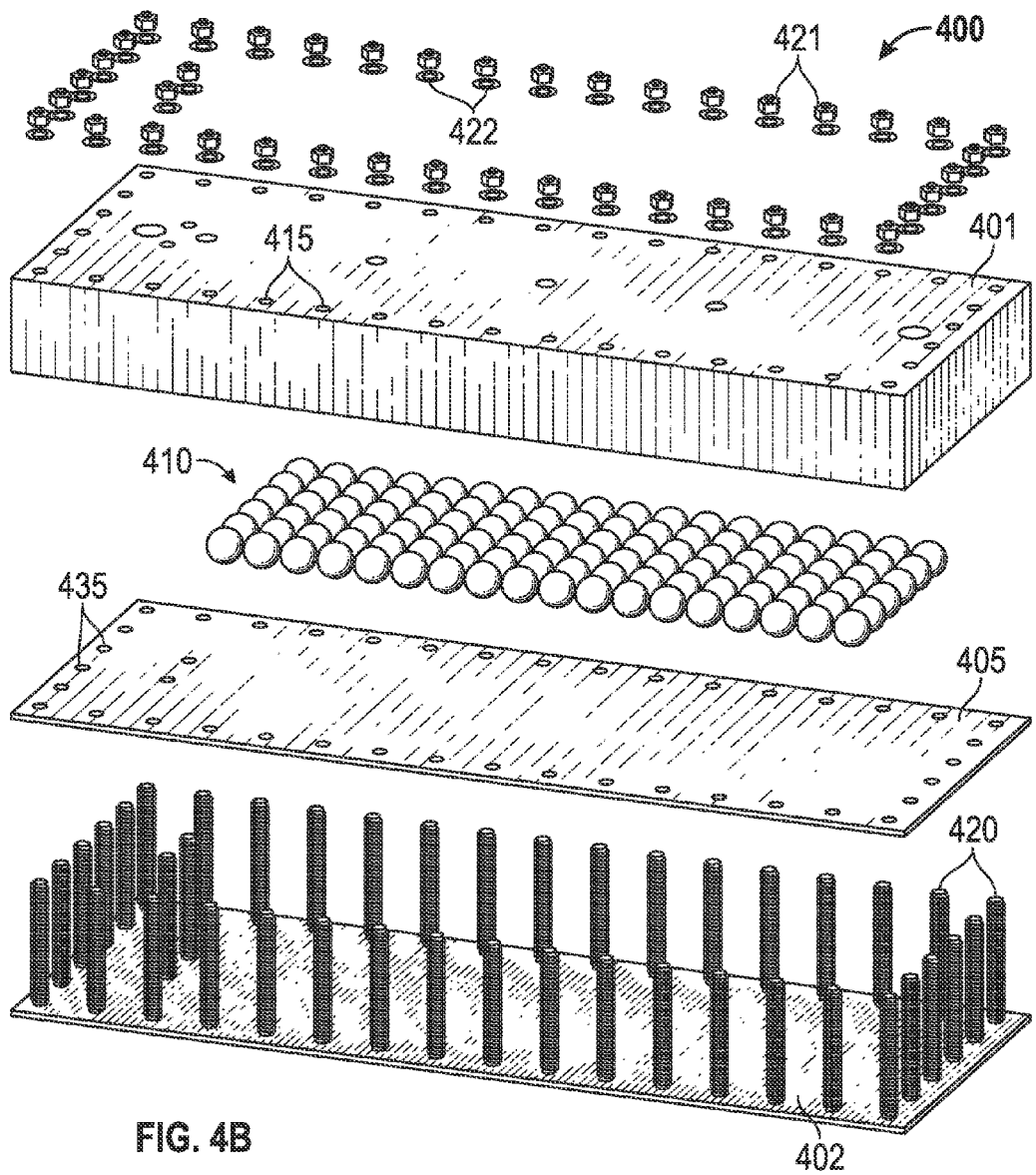
Figure 4C:
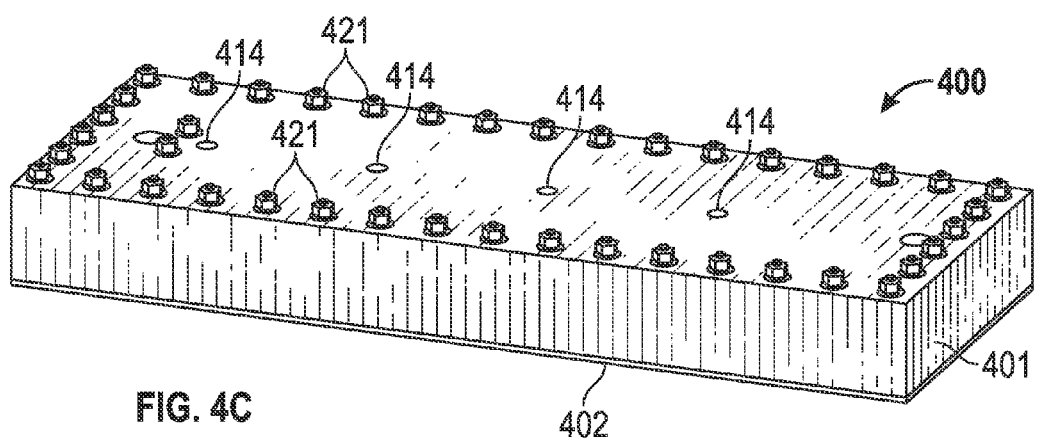
FIG. 4C is an assembled view of the testing system of FIG. 4A-4B.

Referring to FIGS. 4A-4B, exploded views of a first implementation of a testing system 400, in accordance with embodiments disclosed herein, are shown. FIG. 4C is an assembled view of the testing system 400 shown in FIG. 4B. As shown in FIG. 4A, the testing system 400 includes a first plate 401 and a second plate 402. Further as shown, the testing system 400 includes a plurality of spherical testing units 410 and a sealing member 405 disposed between the first plate 401 and the second plate 402. In one or more embodiments, the plurality of spherical testing units may be disposed within a central cavity of the testing system, e.g., within the testing environment 420. As discussed above, the first plate 401 may be formed from a pressure-resistant material allowing at least some transparency, such as acrylic. Further, as discussed above, the second plate 402 may be formed from a substantially rigid material, such as aluminum, for example. In one or more embodiments, the plurality of spherical testing units 410 may be formed from any material known in the art. For example, in one or more embodiments, the spherical testing units 410 may be formed from acrylic. In one or more embodiments, the sealing member 405 may be formed any deformable material known in the art. For example, in one or more embodiments, the sealing member 405 may be formed from rubber and may be a rubber plate disposed between the first plate 401 and the second plate 402.

Although each of the first plate 401, the second plate 402, and the sealing member 405 may appear substantially rectangular in shape as shown in FIGS. 4A-4C, those having ordinary skill in the art will appreciate that each of the first plate 401, the second plate 402, and the sealing member 405 may not necessarily be limited a rectangular shape. For example, in one or more embodiments, each of the first plate 401, the second plate 402, and the sealing member 405 may be circular, elliptical, square, triangular, hexagonal, or any other shape.

In one or more embodiments, the plurality of spherical testing units 410 may be disposed within a central cavity 403 of the testing system 400. In one or more embodiments, the central cavity 403 may be formed on the first plate 401. In one or more embodiments, the plurality of spherical testing units 410 may be configured to fit within the central cavity 403 of the testing system 400 such that clearance between each of the plurality of spherical testing units 410 and the clearance between the plurality of spherical testing units 410 and the surfaces of the first plate 401 are minimized. In other words, in one or more embodiments, a diameter of the spherical testing units 410 may be substantially equivalent to a depth of the central cavity 403 of the testing system 400.

In one or more embodiments, the plurality of spherical testing units 410 may be used to effectively reproduce a porosity of a testing environment, e.g., the central cavity 403 of testing system 400. For example, any gaps that are formed between the plurality of spherical testing units 410 may simulate a porosity of a formation, and a variety of loss control materials (not shown) and/or other fluids (not shown), e.g., drilling mud materials, may be introduced into this controlled, reproducible testing environment and evaluated. Furthermore, gaps formed between the plurality of spherical testing units 410 may be filled with various media to vary the porosity and/or pore space of a simulated formation.

Those having ordinary skill in the art will appreciate that the dimensions of the plurality of spherical testing units 410 as well as the configuration and number of plurality of spherical testing units 410 are not necessarily limited to that shown in FIGS. 4A and 4B. In one or more embodiments, the size and number of the plurality of spherical testing units 410 may be varied to simulate different formations having different porosities and densities. For example, in one or more embodiments, a larger number of smaller spherical testing units 410 may be used to simulate a specific testing environment. Alternatively, in one or more embodiments, a smaller number of larger spherical testing units may be used to simulate a different testing environment. Further, those having ordinary skill in the art will appreciate that the plurality of spherical testing units 410 may not necessarily be uniform in size. For example, in one or more embodiments, the plurality of testing units 410 may be variable in size, e.g., diameters of the spherical testing units 410 may not necessarily be uniform. In other words, in one or more embodiments, spherical testing units 410 of different sizes, i.e., diameter, may be disposed in the testing system 400.

Furthermore, those having ordinary skill in the art will appreciate that the testing system 400 may not necessarily include the plurality of spherical testing units 410. For example, in one or more embodiments, loss control materials and/or other fluids may be introduced into the central cavity 403 of the testing system 400 without any spherical testing units 410 disposed within the central cavity 403. Specifically, testing units to be disposed within the central cavity 403 of the testing system 400 are not limited to spherical testing units 410. For example, in one or more embodiments, a testing unit to be disposed within the central cavity 403 may be oblong, pyramidal, or any other shape known in the art. As such, those having ordinary skill in the art will appreciate that, as a diameter was referenced above regarding the spherical testing units 410, a transverse diameter, conjugate diameter, or height may be referred to regarding the size of testing units of other shapes known in the art, such as an oblong or pyramidal shape.

Alternatively, in one or more embodiments, the testing environment 420 may be manipulated by other components other than the plurality of spherical testing units 410. For example, in one or more embodiments, one or more plates (not shown) configured to fit within the central cavity 403 of the testing system 400 may be disposed within the central cavity 403. A thickness of the plates may alter the available volume within the central cavity 403, which may alter the testing environment 420 for loss control materials and/or other fluids. Those having ordinary skill in the art will appreciate that testing units to be disposed within the central cavity 403 of the testing system 400 may be any component that may affect or alter the available volume within the central cavity 403, which may alter the testing environment 420 for loss control materials and/or other fluids.

Further, in one or more embodiments, the plurality of testing units may include formation samples to be inserted into the testing environment 420. For example, in one or more embodiments, the plurality of testing units may include formation samples such as sand and/or clay. In one or more embodiments, sand samples injected or inserted into the testing environment 420 may be granular, and clay samples may be plate-like in shape. Further, those having ordinary skill in the art will appreciate that any combination of the above-described testing units, e.g., the spherical testing units 410, and formation samples may be injected or inserted into the testing environment 420 to simulate different downhole drilling environments and formation types. For example, in one or more embodiments, a mixture of clay, sand, and/or spherical testing units that vary in diameter may be injected or inserted into the testing environment 420 with or without a fluid.

As discussed above, the first plate 401 may include a plurality of openings 414 formed through a surface of the first plate 401. In one or more embodiments, a plurality of pressure sensors (not shown) may be engaged with the first plate 401 through the plurality of openings 414 and may be configured to monitor pressure within the central cavity 403 of the testing system 400 along a length of the central cavity 403.

Further, as discussed above, the first plate 401 may include a recessed portion 417 formed around the plurality of engagement openings of the first plate 401. In one or more embodiments, the recessed portion 417 may be formed around a perimeter of the top surface of the first plate 401 and the plurality of engagement openings 415 may be formed in the recessed portion 417. In one or more embodiments, the recessed portion 417 may form a lip, or raised edge, around an outer edge of the first plate 401. The recessed portion 417 may provide an area for a deformable sealing member 405 to be disposed, and deform around the lip of the first plate 401, which may provide a pressure-tight seal around the engagement openings of the first plate 401.

In one or more embodiments, the sealing member 405 may be a rubber plate or a gasket, which may be deformed within the recessed portion 417 upon engagement of the first plate 401 and the second plate 402. However, those having ordinary skill in the art will appreciate that the sealing member 405 may be formed from any deformable material known in the art and is not limited to rubber.

In one or more embodiments, the sealing member 405 may include a plurality of engagement openings 435 formed substantially around an outer edge of the sealing member 405. In one or more embodiments, the plurality of engagement openings 435 of the sealing member 405 may be configured to substantially align with the plurality of engagement openings of both the first plate 401 and the second plate 402, such that at least one engagement member (discussed below) may be disposed through each of the first plate 401, the sealing member 405, and the second plate 402. In one or more embodiments, the sealing member 405 may provide a pressure-tight seal around the engagement openings of the first plate 401 and may prevent loss control materials and/or other fluids from inadvertently escaping the central cavity 403 of the first plate 401.

Further, as discussed above, the first plate 401 may be engaged with the second plate 402 by at least one engagement member. In one or more embodiments, the at least one engagement member may be a threaded nut and washer engagement assembly. As shown in FIGS. 4B and 4C, the testing system 400 may include a plurality of threaded rods 420, a plurality of threaded nuts 421, and a plurality of washers 422. In one or more embodiments, the threaded rods 420 may be disposed through engagement openings formed in each of the first plate 401 and the second plate 402, respectively. Once the threaded rods 420 are disposed through the engagement openings of each of the first plate 401 and the second plate 402, washers 422 may be disposed over the threaded rods 420 and the threaded nuts 421 may be threaded onto the threaded rods 420, as shown in FIG. 4C.

Alternatively, in one or more embodiments, the testing system 400 may not include threaded rods 420, threaded nuts 421, and washers 422. Those having ordinary skill in the art will appreciate that the first plate 401 may be engaged with the second plate 402 by any means known in the art and may not be limited to a threaded engagement through threaded rods 420 and threaded nuts 421. For example, in one or more embodiments, the first plate 401 may be securely engaged to the second plate 402 by way of one or more clamps, such as a pneumatic clamp, bonding agents, or any other engagement means known in the art.

Figure 5A:
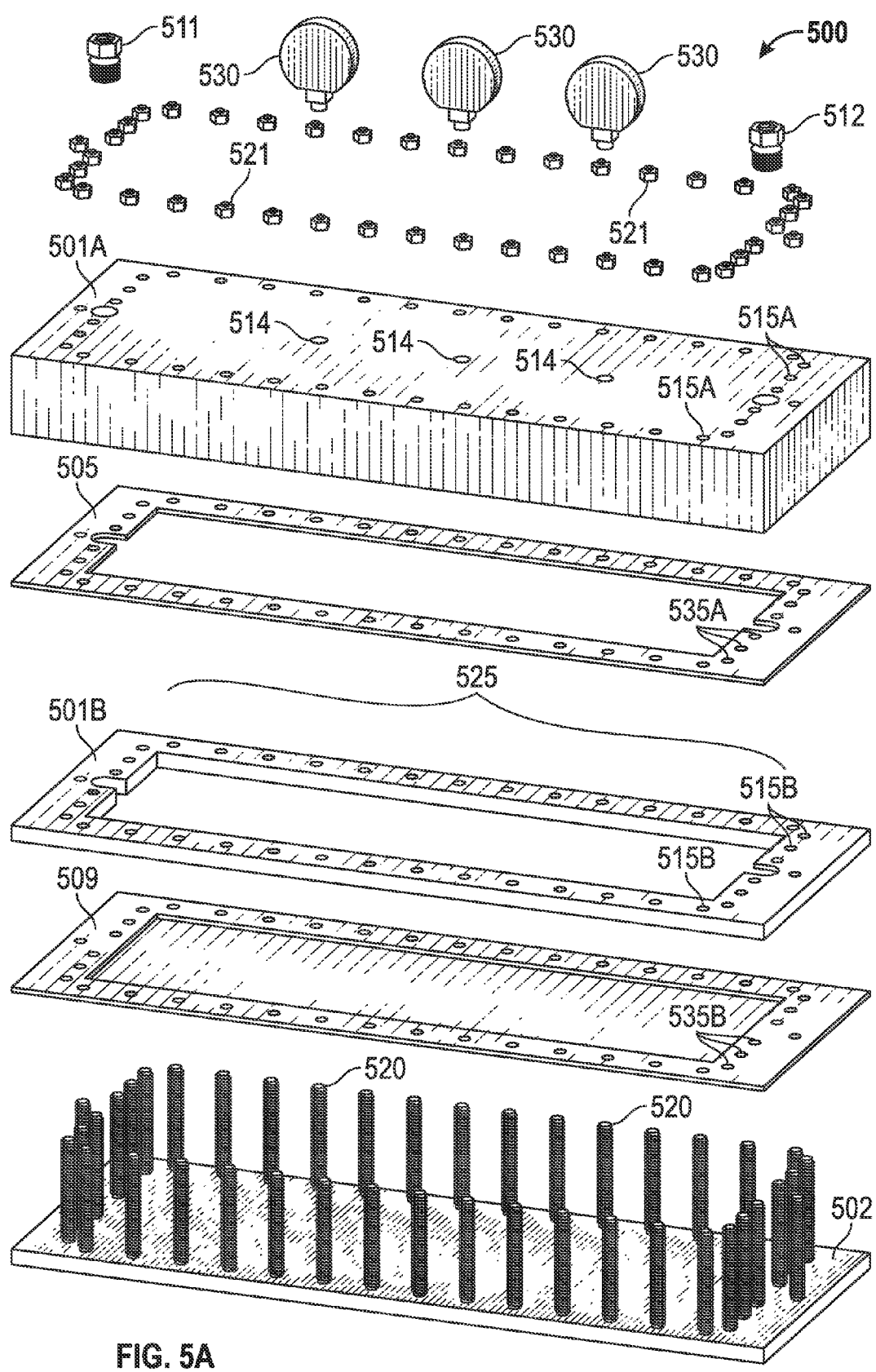
FIG. 5A is an exploded view of a second implementation of a testing system according to embodiments of the present disclosure.
Figure 5B:
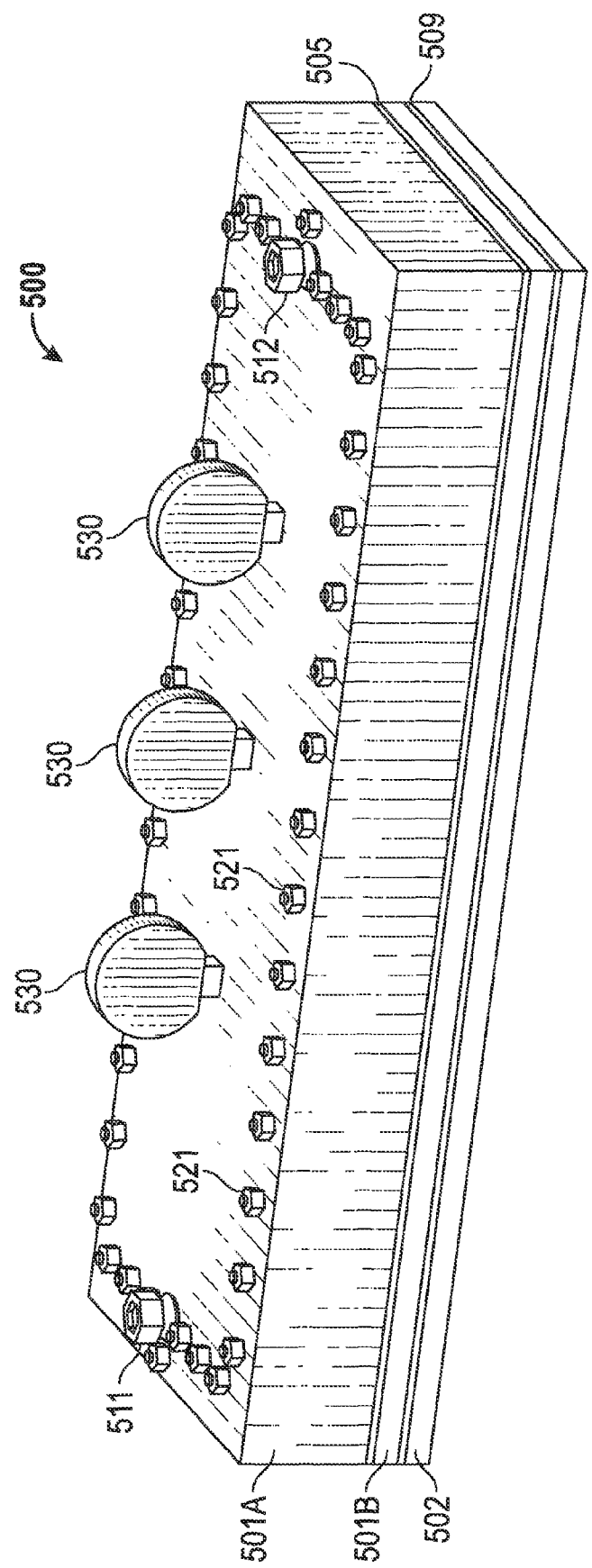
FIG. 5B is an assembled view of the testing system of FIG. 5A.
Figure 5C:
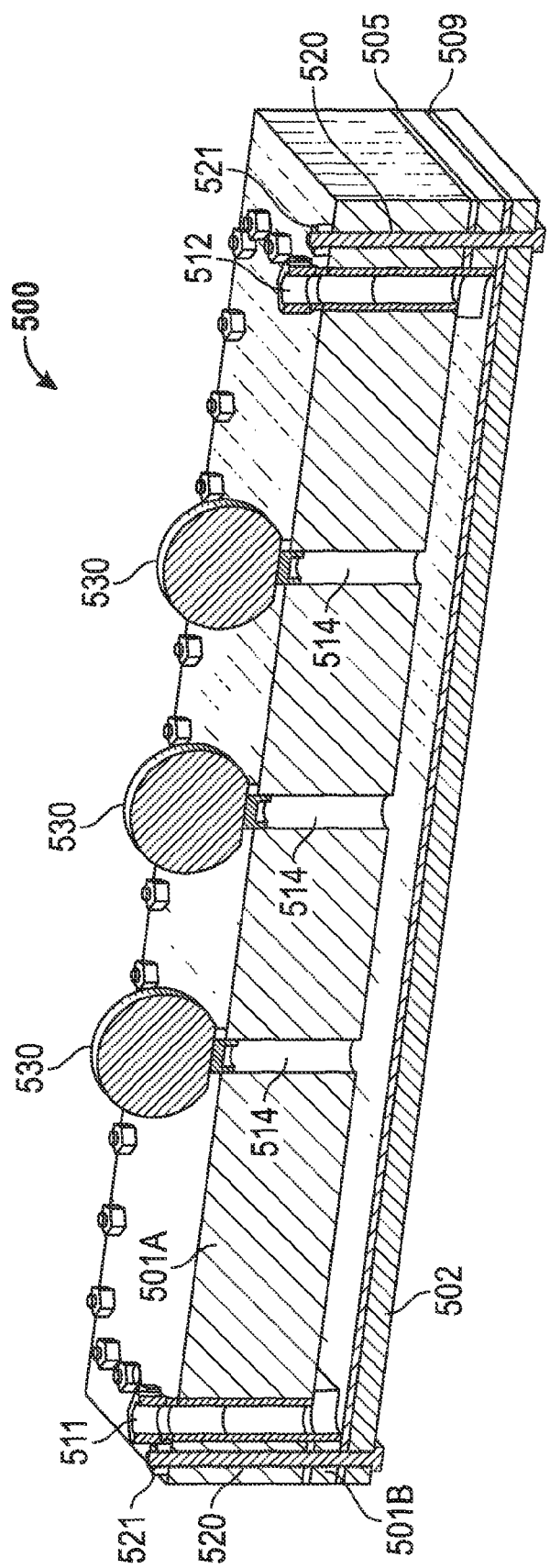
FIGS. 5C-5D are multiple cross-sectional views of the assembled testing system of FIG. 5B.
Figure 5D:
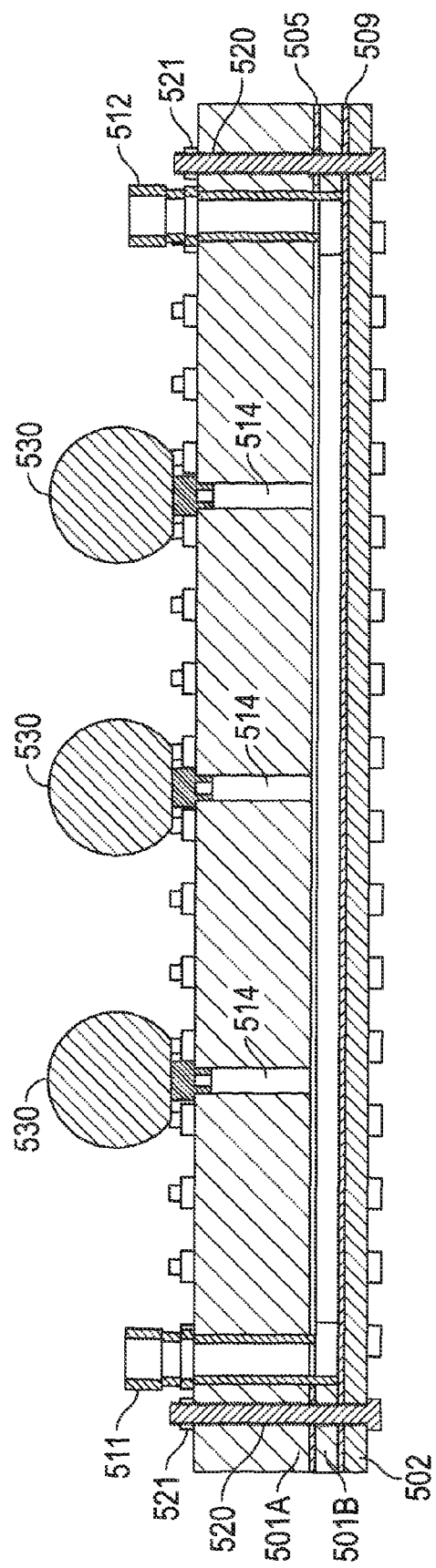

Referring to FIG. 5A, an exploded view of a second implementation of a testing system 500, in accordance with embodiments disclosed herein, is shown. FIG. 5B is an assembled view of the testing system 500, and FIGS. 5C-5D are cross-sectional views of the assembled testing system 500B. As shown in FIG. 5A, the testing system 500 may include a first plate 501A, an intermediate plate 501B, and a second plate 502. As discussed above, the first plate 501A may be formed from a pressure-resistant, substantially transparent (i.e., allowing at least some transparency) material, such as acrylic. In one or more embodiments, the substantially transparent material of the first plate 501A may allow a user to visually inspect and monitor a fluid (not shown) on the surface of the second plate 502 (described below). For example, the substantial transparency of the first plate 501A may allow a user to visually inspect and monitor a profile and/or flow of a fluid that is disposed within the testing environment 525 of the intermediate plate 501B, such as along the surface of the second plate 502. Further, as discussed above, the second plate 502 may be formed from a substantially rigid material, such as aluminum. In one or more embodiments, the intermediate plate 501B may be formed from either a pressure-resistant substantially transparent material, such as acrylic, or a substantially rigid material, such as aluminum.

In one or more embodiments, a first sealing member 505 may be disposed between the first plate 501A and intermediate plate 501B. Further, a second sealing member 509 may be disposed between the intermediate plate 501B and the second plate 502. In one or more embodiments, each of the first sealing member 505 and the second sealing member 509 may be formed from any deformable material known in the art. For example, in one or more embodiments, each of the first sealing member 505 and the second sealing member 509 may be formed from a deformable or elastic material, such as rubber, and may be a rubber plates, for example, disposed between each of the first plate 501A, the intermediate plate 501B, and the second plate 502. However, those having ordinary skill in the art will appreciate that each of the first sealing member 505 and the second sealing member 509 may be formed from any deformable material known in the art and is not limited to rubber.

In one or more embodiments, each of the intermediate plate 501B and the second sealing member 509 may have a central opening formed therethrough. As shown, the intermediate plate 501B may form a perimeter around the central opening formed through the intermediate plate 501B. Similarly, the second sealing member 509 may form a perimeter around the central opening formed through the second sealing member 509. In one or more embodiments, when the first plate 501A, intermediate plate 501B, and second plate 502 are stacked together, the central opening formed through the intermediate plate 501B may form a central cavity in the testing system 500. In one or more embodiments, the central cavity of the testing system 500 may be a testing environment 525 along the surface of the second plate 502 for the testing system 500.

In one or more embodiments, a plurality of spherical testing units (not shown) may be disposed within the central cavity of the testing system 500. Although not shown in FIGS. 5A-5D, spherical testing units 410 described previously may be utilized in the testing system 500. In one or more embodiments, the plurality of spherical testing units may be configured to fit within the testing environment 525 such that clearance between each of the plurality of spherical testing units and the clearance between the plurality of spherical testing units and the surfaces of the first plate 501A and the intermediate plate 501B are minimized. In other words, in one or more embodiments, a diameter of the spherical testing units may be substantially equivalent to a thickness of the intermediate plate 501B.

As discussed above, the first plate 501A may include a plurality of openings 514 formed through a surface of the first plate 501A. In one or more embodiments, a plurality of pressure sensors 530 may be engaged with the first plate 501A through the plurality of openings 514 and may be configured to monitor pressure within the testing environment 525, e.g., within the hole formed through the intermediate plate 501B along a length of the first plate 501A and/or the intermediate plate 501B.

In one or more embodiments, each of the first sealing member 505 and the second sealing member 509 may include a plurality of engagement openings 535A and 535B, respectively, formed substantially around an outer edge of each of the first sealing member 505 and the second sealing member 509. In one or more embodiments, the first plate 501A may include engagement openings 515A and the intermediate plate 501B may include engagement openings 515B. In one or more embodiments, the plurality of engagement openings 535A and 535B may be configured to substantially align with the plurality of engagement openings of each of the first plate 501A, the intermediate plate 501B, and the second plate 502 such that at least one engagement member (discussed below) may be disposed through each of the first plate 501A, the first sealing member 505, the intermediate plate 501B, the second sealing member 509, and the second plate 502. In one or more embodiments, each of the first sealing member 505 and the second sealing member 509 may provide a pressure-tight seal around the engagement openings of the first plate 501A and may prevent loss control materials and/or other fluids, e.g., drilling mud materials and/or water, from inadvertently escaping the testing environment 525 of the testing system 500.

Further, as discussed above, the first plate 501A may be engaged with the second plate 502 by at least one engagement member. In one or more embodiments, the at least one engagement member may be a threaded nut engagement assembly. As shown, the testing system 500 may include a plurality of threaded rods 520 and a plurality of threaded nuts 521. In one or more embodiments, the threaded rods 520 may be disposed through engagement openings formed in each of the first plate 501A, the intermediate plate 501B, and the second plate 502, respectively. Once the threaded rods 520 are disposed through the engagement openings of each of the first plate 501A, the intermediate plate 501B, and the second plate 502, the threaded nuts 521 may be threaded onto the threaded rods 520.

In one or more embodiments, the testing system 500 may include an inlet 511 and an outlet 512. In one or more embodiments, each of the inlet 511 and the outlet 512 may be openings formed into, for example, the first plate 501A, the first sealing member 505 and/or the intermediate plate 501B. In one or more embodiments, fluid communication may be provided between each of the inlet 511 and the outlet 512 through the central cavity of the testing system 500 or the testing environment 525. As discussed above, in one or more embodiments, the central cavity of the testing system 500 may include the central opening formed through the intermediate plate 501B. Alternatively, in one or more embodiments, the central cavity of the testing system 500 may include a central cavity (not shown) that may be formed in the first plate 501A. In one or more embodiments, each of the inlet 511 and the outlet 512 may extend in directions that are substantially orthogonal to a fluid flow path through the central cavity of the testing system 500, which may be between the inlet 511 and the outlet 512.

As discussed in detail above, the testing environment 525 may be manipulated to simulate different downhole drilling environments as well as formation types. In one or more embodiments, the testing environment 525 may be manipulated by testing units, e.g., the spherical testing units 410 shown in FIGS. 4A and 4B, which may be used to simulate a vugular formation. Alternatively, as discussed above, the testing units may not necessarily be included in the testing system 500 and one or more fluids described above may be displaced across the testing environment, e.g., a cavity formed in the first plate 501A or a hole formed through the intermediate plate 501B, without the testing units, which may simulate a fracture. Alternatively, in one or more embodiments, the testing environment 525 of the testing system 500 may be manipulated to simulate depleted formation types or sand formation types. For example, the testing environment 525 of the testing system 500 may include sands (not shown) or other testing units (not shown) to help simulate specific testing environments, such as depleted formation types.

According to another aspect, there is provided a method of manufacturing a testing system, the method including forming a cavity on a first plate, forming an inlet, an outlet, and a plurality of openings formed through a surface of the first plate, and forming a plurality of engagement openings through the first plate and a second plate. Referring back to FIG. 1, the first plate 101 includes the cavity 103 formed therein, as well as the inlet 111, the outlet 112, and the plurality of openings 114 formed through a surface of the first plate 101. Further, as shown in FIG. 1, the first plate 101 also includes a plurality of engagement openings 115 formed substantially around an outer edge of the first plate 101.

As shown in FIG. 3, the second plate 301 includes the plurality of engagement openings 325 formed substantially around an outer edge of the second plate 301. Those having ordinary skill in the art will appreciate that the cavity 103, inlet 111, outlet 112, and the plurality of engagement openings 115 and 325 may be formed in each of the first plate 101 and the second plate 302, respectively, by any means known in the art. For example, the cavity 103, inlet 111, outlet 112, and the plurality of engagement openings 115 and 325 of each of the first plate 101 and the second plate 302, respectively, may be formed by any milling, molding, cutting, or pressing process known in the art.

The method may include forming a hole through an intermediate plate, in which the intermediate plate forms a perimeter around the hole. The method may also include engaging the first plate, the intermediate plate, and the second plate with at least one engagement member. As shown in FIGS. 5A-5D, the intermediate plate 501B has a hole formed therethrough and a plurality of engagement openings formed therethrough. Further, as shown the threaded rods 520 may be disposed through engagement openings formed in each of the first plate 501A, the intermediate plate 501B, and the second plate 502, respectively. Once the threaded rods 520 are disposed through the engagement openings of each of the first plate 501A, the intermediate plate 501B, and the second plate 502, the threaded nuts 521 may be threaded onto the threaded rods 520.

The method may also include engaging the first plate with the second plate with at least one engagement member, and coupling a plurality of pressure sensors with the plurality of openings of the first plate. As shown in FIG. 4C, the first plate 401 is engaged with the second plate 402 with at least one threaded nut 421. As discussed above, in one or more embodiments, the at least one engagement member may also include at least one threaded rod 420 and at least one washer 422 that is configured to engage with the plurality of engagement openings formed through each of the first plate 401 and the second plate 402. Although not shown, those having ordinary skill in the art will appreciate that a plurality of pressure sensors (not shown) may be coupled to the first plate 401 through the plurality of openings 414 by any means known in the art. For example, in one or more embodiments, a portion of the plurality of pressure sensors may be disposed through each of the plurality of openings 414 and may be configured to monitor pressure within the cavity of the first plate 401. The multiple pressure sensors may allow users to monitor pressure transmission of fluids, such as mud, against loss circulation materials in a simulated formation.

Further, the method may also include forming a plurality of spherical testing units configured to be disposed within the cavity of the first plate 501A. The plurality of spherical testing units, shown as 410 in FIGS. 4A and 4B, and which may also be applicable to FIGS. 5A-5D, may be formed by any means or method known in the art. The plurality of spherical testing units 410 may be formed from any substantially rigid material known in the art. For example, in one or more embodiments, the plurality of spherical testing units 410 may be formed from acrylic, steel, or any other metal known in the art. As such, the plurality of spherical testing units 410 may be formed by a casting process, molding process, or any other process known in the art.

Furthermore, the method may include forming a sealing member and engaging the sealing member between the first plate and the second plate. As shown in FIG. 4B, for example, the sealing member 405 may be formed to engage around an outer edge of each of the first plate 401 and the second plate 402. Further, as discussed above, the sealing member 405 may be formed from a deformable or elastic material such as rubber, for example, and may be a rubber plate or gasket disposed between the first plate 401 and the second plate 402. Furthermore, as discussed above, the sealing member 405 may include a plurality of engagement openings 435 formed substantially around an outer edge of the sealing member 405. In one or more embodiments, the plurality of engagement openings 435 of the sealing member 405 may be configured to substantially align with the plurality of engagement openings of both the first plate 401 and the second plate 402. Those having ordinary skill in the art will appreciate that the deformable sealing member 405 and the plurality of engagement openings 435 of the sealing member 405 may be formed by any means known in the art. For example, the deformable sealing member 405 and the plurality of engagement openings 435 of the sealing member 405 may be formed by a molding or pressing process, and the engagement openings 435 of the sealing member 405 may be punched or cut out of the perimeter of the sealing member 405.

For example, referring briefly to FIG. 4A, a testing system 400 may include a first plate 401, a second plate 402, and a plurality of pressure sensors (not shown) engaged with the first plate 401 through a plurality of openings 414 formed in the first plate 401. As shown in FIG. 1, a first plate 101 may also include an inlet 111 and an outlet 112, which may be configured to introduce and receive a fluid, respectively.

Further, referring briefly to FIG. 5A, although not shown, in one or more embodiments, a testing system 500 may include a fluid circulation outlet (not shown). In one or more embodiments, the fluid circulation outlet may be an opening formed into, for example, the second plate 502 and the second sealing member 509. In one or more embodiments, the fluid circulation outlet may be in fluid communication with the central cavity of the testing system 500. Further, in one or more embodiments, the fluid circulation outlet may be in fluid communication with the inlet 511. In one or more embodiments, the fluid circulation outlet may form a part of the inlet 511 such that the inlet 511 may effectively extend through each of the first plate 501A, the intermediate plate 501B, and the second plate 502. In one or more embodiments, the fluid circulation outlet may extend in a direction that is substantially opposite to the inlet direction and that is substantially orthogonal to a fluid flow path through the central cavity of the testing system 500, which may be between the inlet 511 and the outlet 512.

In one or more embodiments, one or more fluids may flow through the central cavity of the testing system in a substantially horizontal direction. In one or more embodiments, fluid communication may be provided between the inlet and the outlet of the testing system through the central cavity of the testing system. As such, in one or more embodiments, a fluid flow path through the central cavity of the testing system may be in a substantially horizontal direction. In one or more embodiments, the inlet and the outlet may extend in substantially vertical directions. In other words, in one or more embodiments, the inlet and the outlet may extend in directions that are substantially orthogonal to a fluid flow path through the central cavity of the testing system. As such, in one or more embodiments, a loss control and/or one or more fluids may be circulated through the inlet and the outlet of the testing system in a direction that is substantially orthogonal to a fluid flow path through the testing environment of the testing system.

Figure 6:
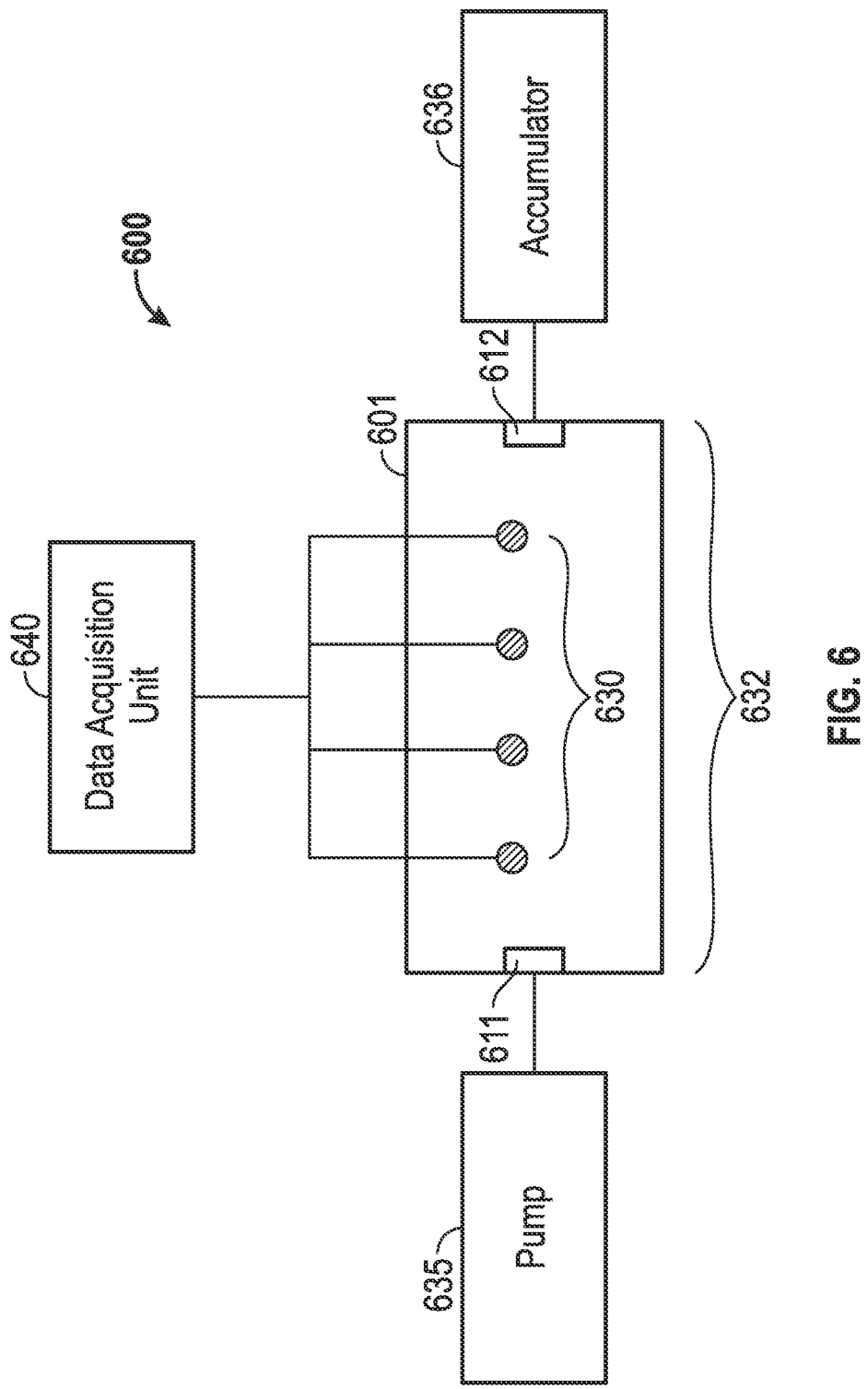
FIG. 6 is a schematic diagram of the testing system of FIG. 5A.

Referring now to FIG. 6, a schematic diagram of a testing system 600, according to embodiments disclosed herein, such as FIGS. 5A-5D, is shown. As shown, the testing system 600 includes a first plate 601 having an inlet 611 at a first end, an outlet 612 at a second end, and a plurality of pressure sensors 630 engaged with the first plate 601, in which the plurality of pressure sensors 630 are distributed between the first end and the second end of the first plate 601. As discussed above, a pump 635 may be coupled to an inlet 611 formed on a first end of the first plate 601. In one or more embodiments, the pump 635 may be configured to pump or inject a fluid (not shown) into the inlet 611 of the first plate 601.

Further, as discussed above, an accumulator 636 may be coupled to the outlet 612 formed on a second end of the first plate 601. In one or more embodiments, the accumulator 636 may be configured to collect and receive a fluid that is injected into the central cavity (not shown) of the testing system 600 through the outlet 612. For example, in one or more embodiments, the accumulator 636 may collect and receive a fluid, e.g., loss control material, water, and/or drilling mud material, through the outlet 612 of the first plate 601.

Further, as shown, the plurality of pressure sensors 630 are engaged with the first plate through a plurality of openings (not shown) formed in the first plate 601. The pressure sensors 630 may be configured to monitor and collect data regarding a pressure of a fluid (not shown) within the testing environment.

Furthermore, in one or more embodiments, the data acquisition unit 640 may be operatively coupled to the plurality of pressure sensors 630. In one or more embodiments, the data acquisition unit 640 may be configured to record and store data collected by the plurality of pressure sensors 630. For example, in one or more embodiments, the data acquisition unit 640 may store and organize pressure data according to different fluids and according to different testing environments, which may be manipulated by testing units, e.g., spherical testing units 410 shown in FIGS. 4A and 4B. Those having ordinary skill in the art will appreciate that the data acquisition unit 640 may be any unit known in the art that is capable of receiving, handling, recording, storing, transferring, and/or processing data collected by the plurality of pressure sensors 630.

Correspondingly, the data acquisition unit 640 may also collect time and location data in addition to pressure data, for example, collected by the plurality of pressure sensors 630. For example, in one or more embodiments, the data acquisition unit 640 may store and organize data regarding the time it may take to inject a loss control material into the testing environment 632 before the loss control material is set and a barrier is formed by the loss control material within the testing environment 632. Further, in one or more embodiments, the data acquisition unit 640 may store and organize data regarding a location within the testing environment 632 at which a loss control material becomes set and forms a barrier.

Figure 7:
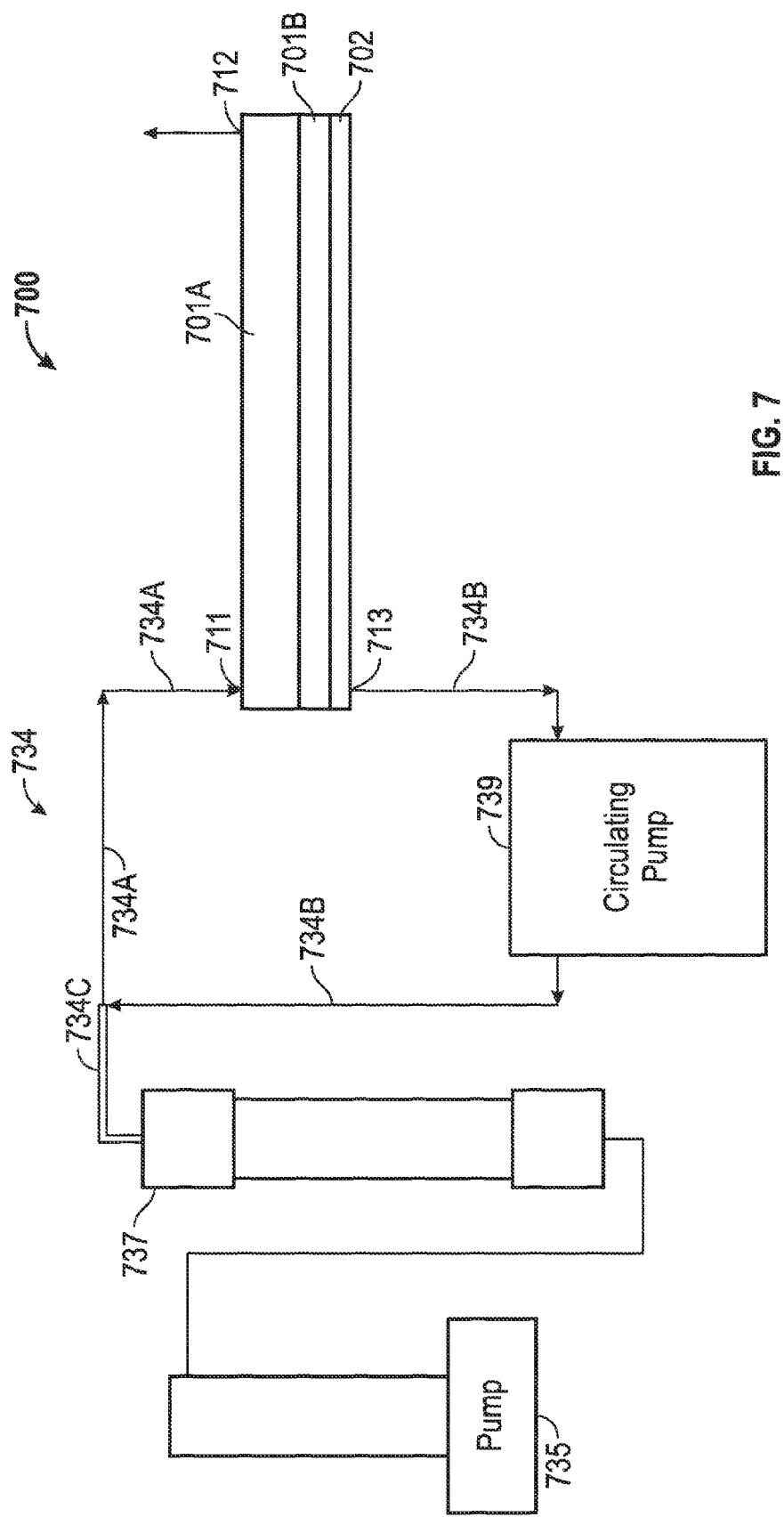
FIG. 7 is another schematic diagram of the testing system of FIG. 5A.
Figure 8:
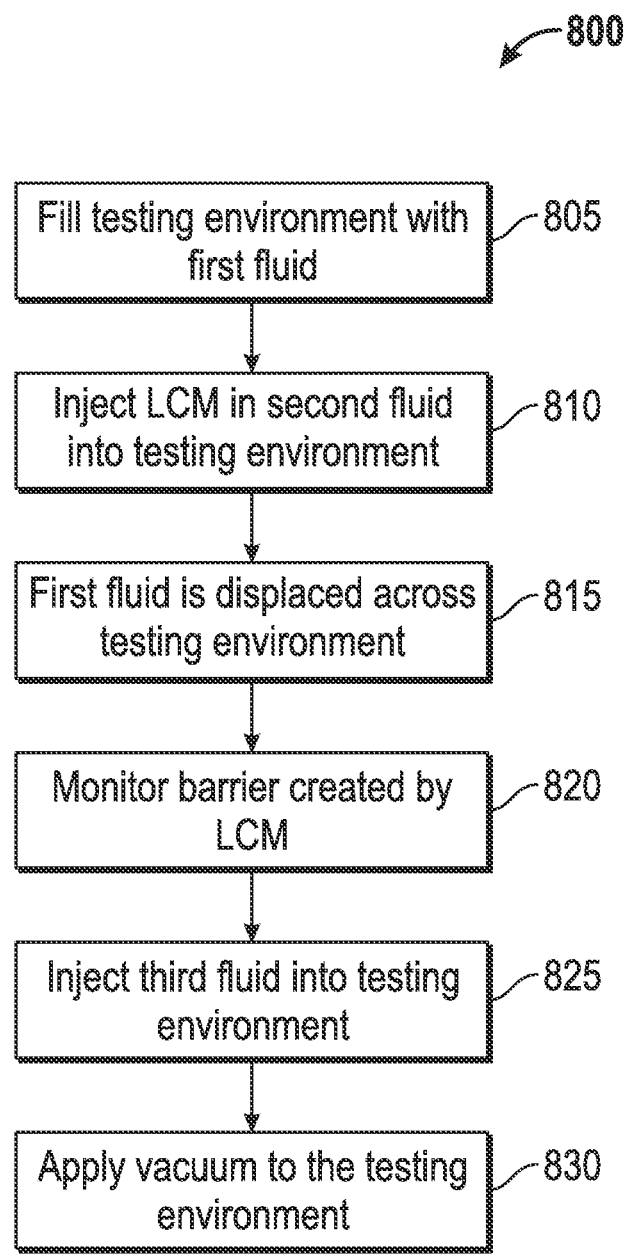
FIG. 8 is a flowchart of a method according to embodiments of the present disclosure.

Turning to FIG. 7, a schematic diagram of a testing system 700, in accordance with embodiments disclosed herein, is shown. As shown, the testing system 700 includes a first plate 701A having an inlet 711, an outlet 712, and a plurality of pressure sensors (not shown) engaged with the first plate 701A. In one or more embodiments, the pump 735 may be configured to pump or inject a fluid (not shown) into the inlet 711 of the first plate 701A.

The testing system 700 shown in FIG. 7 is that illustrated in and described below in greater detail with respect to FIGS. 5A-D. However, it is also contemplated that there be variations and/or modifications in the arrangement of plates, etc., in the testing system 700 and may include an arrangement as illustrated in FIGS. 1-4.

An accumulator (not shown) may be coupled to the outlet 712 formed on a second end of the first plate 701A. In one or more embodiments, the accumulator may be configured to collect and receive a fluid that is injected into the central cavity (not shown) and flows out of the testing system 700 through the outlet 712. For example, in one or more embodiments, the accumulator may collect and receive a fluid, (e.g., loss control material, water, and/or drilling mud material) through the outlet 712 of the first plate 701A such as the first fluid, the second fluid, and/or the third fluid.

Further, as discussed above, a plurality of pressure sensors (not shown) are engaged with the first plate through a plurality of openings (not shown) formed in the first plate 701A. The pressure sensors may be configured to monitor and collect data regarding a pressure of a fluid (not shown) contained within the central cavity of the testing system 700. As discussed above, in one or more embodiments, a data acquisition unit (not shown) may be operatively coupled to the plurality of pressure sensors. In one or more embodiments, the data acquisition unit may be configured to receive, handle, record, store, transfer, and/or process data collected by the plurality of pressure sensors.

In one or more embodiments, a circulation line 734 may be coupled to the inlet 711 formed on the first plate 701A and a circulation outlet 713 formed on the second plate 702. As discussed above, in one or more embodiments, an opening including the inlet 711 may be formed through each of the first plate 701A and the second plate 702 such that the opening also includes the circulation outlet 713 formed on the second plate 702. In one or more embodiments, a fluid, e.g., a drilling mud material and/or water, and/or a fluid loss material may be circulated through the circulation line 734, which may be circulated with a circulating pump 739. Those having ordinary skill in the art will appreciate that the circulating pump 739 may be any pump known in the art or any mechanism known in the art that may circulate a fluid through the circulation line 734.

Circulation line 734, in particular, the flow of fluid into inlet 711 through circulation outlet 713 may simulate the pumping/circulation of a wellbore fluid through a wellbore formed through an earthen formation. Further, in one or more embodiments, the testing environment, e.g., a central cavity formed in the testing system 700, may simulate the earthen formation through which the wellbore is drilled, and into which one or more fluids in a wellbore, e.g., a loss control material, water, and/or drilling mud material, may penetrate. As discussed in greater detail below, the testing environment may be manipulated to simulate different downhole drilling environments as well as formation types. For example, the testing environment of the testing system 700 may include sands (not shown) or other testing units (not shown) to help simulate specific testing environments, such as depleted formation types.

In one or more embodiments, the circulation line 734 may be divided into three sections, which include 734A, 734B, and 734C. In one or more embodiments, section 734A of the circulation line 734 may represent a flow of fluid circulated into the inlet 711 formed on the first plate 701A. In one or more embodiments, section 734B of the circulation line 734 may represent an amount of fluid circulated out of the circulation outlet 713 formed on the second plate 702 (i.e., less any fluid "lost" to the "formation" or central cavity of the testing system 700). In one or more embodiments, section 734C of the circulation line 734 may represent flow in either direction, depending on whether there is excess fluid in circulation or whether substantial amounts of fluid is lost to the formation such that an additional volume of fluid is used for the desired pump rates. In one or more embodiments, the amount of fluid represented by section 734A of the circulation line 734 may be substantially equivalent to the total amount of fluid and/or loss control material represented by both section 734B and section 734C of the circulation line 734. In one or more embodiments, the fluid being circulated through the circulation line 734 may include a loss control material.

Further, in one or more embodiments, the circulation of a fluid through the circulation line 734, e.g., through sections 734A and 734B of the circulation line 734, may simulate a wellbore and the flow of one or more fluids in a wellbore environment. For example, in one or more embodiments, fluid flow through the circulation line 734 from the inlet 711 to the circulation outlet 713 may simulate a wellbore and fluid flow in a wellbore environment.

As discussed above, in one or more embodiments, each of the inlet 711 and the outlet 712 may extend in directions that are substantially orthogonal to a fluid flow path through the central cavity of the testing system 700, which may be between the inlet 711 and the outlet 712. In one or more embodiments, the fluid circulation outlet 713 may extend in a direction that is substantially opposite to the inlet 711 direction and that is substantially orthogonal to a fluid flow path through the central cavity of the testing system 700, which may be between the inlet 711 and the outlet 712.

In one or more embodiments, the fluid circulation outlet 713 may form a part of the inlet 711 such that the opening that forms the inlet 711 may effectively extend through each of the first plate 701A and the second plate 702. As such, in one or more embodiments, the opening that forms the inlet 711 on the first plate 701A may also form the circulation outlet 713 formed on the second plate 702. Alternatively, in one or more embodiments, the opening that forms the inlet 711 on the first plate 701A may not necessarily form the circulation outlet 713 formed on the second plate. In other words, in one or more embodiments, although the inlet 711 and the circulation outlet 713 may be in fluid communication, the circulation outlet 713 may not necessarily be formed from the same opening as the inlet 711. Depending on the arrangement of the testing system 700, the fluid flow path may also extend through any plates intermediate the first plate 701A and second plate 702, such as an intermediate plate 701B. Thus, for example, aligned through holes (not shown) may extend through the first plate 701A and second plate 702, and may open into the central cavity of the testing at some axial location between inlet 711 and circulation outlet 713 (such as at an intermediate plate 701B).

Further, in one or more embodiments, a pressure differential may be maintained across each of the first plate 701A, the intermediate plate 701B, and the second plate 702 such that, as one or more fluids are circulated through the circulation line 734, the one or more fluids circulated through the circulation line 734 may be displaced, e.g., displaced horizontally, across the central cavity of the testing system 700. In one or more embodiments, a back-pressure regulator (not shown) or pump (not shown) may be coupled to the outlet 712 to help maintain a pressure differential across each of the first plate 701A, the intermediate plate 701B, and the second plate 702.

In one or more embodiments, the one or more fluids circulated in the circulation line 734 may be circulated at a higher pressure to simulate overbalanced drilling until a seal is made. For example, in one or more embodiments, one or more fluids circulated in the circulation line 734 may be circulated at a higher pressure to simulate overbalanced drilling until a barrier is formed by a loss control material (not shown) within the testing environment of the testing system 700. In one or more embodiments, when a barrier is made within the testing environment of the testing system 700, a loss control material may be said to have set, which may not allow fluids to be displaced beyond the point in the testing environment at which the loss control material is set. In one or more embodiments, when a loss control material is set, fluids may still be able to be displaced beyond the point in the testing environment at which the loss control material is set. However, the rate at which the fluids are displaced beyond the set loss control material may be reduced as a result of the set loss control material. As a result of the setting of a loss control material, in one or more embodiments, a pressure within the testing environment between the inlet 711 and the point at which the loss control material is set may be higher than a pressure within the testing environment between the point at which the loss control material is set and the outlet 712.

In one or more embodiments, a circulation accumulator 737 may be operatively connected between the pump 735 and the circulation line 734 and may accumulate any excess fluid and/or loss control material from the circulation line 734. Accumulator 737 may comprise a floating piston (not shown) separating the pump fluid (e.g., water) and the injection fluid (i.e., product being tested). As shown in FIG. 7, the pump 735 may pressurize the accumulator 737, thus causing a floating piston of the accumulator 737 to force the injection fluid into the first plate 701A of the testing system 700.

As discussed above, the method 800 for testing a loss control material may include filling 805 a testing environment in a testing system with a first fluid. In one or more embodiments, the testing environment of the testing system may be a central cavity formed in the testing system between the first plate and a second plate of a testing system. The method for testing a loss control material may also include injecting 810 a loss control material in a second fluid into the testing system, such as drilling mud material and/or water. For example, in one or more embodiments, the loss control material may be injected into the testing environment of the testing system through the inlet 611 with the pump 635, as seen in FIG. 6. In one or more embodiments, the inlet 611 may be located on a first end of the testing system. In one or more embodiments, the loss control material may be injected into the testing system without another fluid, i.e., without the second fluid.

In one or more embodiments, as the loss control material is injected into the testing environment with the second fluid, the first fluid may be displaced 815 across the testing environment to a second end of the testing system. Further, in one or more embodiments, a third fluid may be injected into the testing environment. The pump may be used to inject other fluids into the testing system. For example, in one or more embodiments, the pump may be used to inject the first fluid, the second fluid, and/or the third fluid into the testing system. In one or more embodiments, each of the first fluid, the second fluid, and the third fluid may be a drilling mud material and/or water. Those having ordinary skill in the art will appreciate that more than three fluids may be injected into the testing environment of the testing system. For example, in one or more embodiments, one, two, three, four, five or more fluids may be injected into the testing environment of the testing system.

The method may also include monitoring 820 a barrier created by the loss control material while the loss control material is injected into the testing system. Further, the method may also include visually monitoring the fluid while the fluid is injected into the testing system. As discussed above, in one or more embodiments, the first plate may be formed from a pressure-resistant substantially transparent (i.e., allowing at least some transparency) material such as acrylic and the like. As such, in one or more embodiments, in addition to monitoring pressure within the central cavity of the testing system via the plurality of pressure sensors, a user may visually inspect and monitor a profile of the loss control material or the fluid that is injected into the testing system, e.g., injected into the central cavity of the testing system. For example, in one or more embodiments, a user may visually monitor gel formation, defluidization, and/or compaction or filtercake formation.

In one or more embodiments, injecting the third fluid 825 into the testing environment may be a stepped injection. For example, in one or more embodiments, the amount of the third fluid and the rate of injection of the third fluid into the testing environment may vary, e.g., may increase or decrease, during the injection of the third fluid. In other words, the amount of the third fluid and the rate of injection of the third fluid into the testing environment may be stepped up or stepped down at various points during the injection of the third fluid. In one or more embodiments, the amount of the third fluid and the rate of injection of the third fluid may be controlled by a user based on feedback received by a data acquisition unit (described above), the plurality of pressure sensors, or according to a user. As such, one having ordinary skill in the art will appreciate that the pump may be controlled by a user such that the amount of fluid and a rate of injection of the fluid may be controlled by a user.

The method may also include applying a vacuum 830 to the testing system. In one or more embodiments, the central cavity of the first plate may be put into a vacuum before any fluids are introduced into the testing system. Further, in one or more embodiments, water and/or drilling mud material may be injected or flushed through the testing system, e.g., into the cavity of the first plate. This water and/or drilling mud material may be flushed through the testing system to remove any air within the testing system. Once the system is flushed, according to one or more embodiments, the loss control material may be injected into the system, followed by the injection of the fluid, e.g., drilling mud materials and/or water. Those having ordinary skill in the art will appreciate that loss control materials, according to embodiments disclosed herein, may include solid-based loss control materials, polymeric loss control materials, cement-based loss control material, or any other loss control material known in the art. Further, those having ordinary skill in the art will appreciate that the loss control material may be injected into the testing system simultaneously with other fluids, e.g., the second fluid, such as drilling mud material or water.

The method for testing a loss control material may include injecting a first fluid into the testing system, e.g., into a testing environment or central cavity formed in the testing system, with the pump. Although not shown in FIG. 7, the testing environment and central cavity of testing system may be analogous to the testing environment 632 seen in FIG. 6. In one or more embodiments, the first fluid may be a drilling mud material, water, or a combination thereof. In one or more embodiments, a loss control material may be injected into the test system with a second fluid, which may also include drilling mud material or water. Alternatively, in one or more embodiments, the loss control material may be injected into the testing system without another fluid. Further, the pump may be used to inject a third fluid into the testing system. In one or more embodiments, the third fluid may be a drilling mud material. Alternatively, in one or more embodiments, the fluid may be water or a loss control material.

Those having ordinary skill in the art will appreciate that, according to one or more embodiments, collecting data from the plurality of pressure sensors as well as visually monitoring the loss control material and/or other fluid may be across the entire length of the testing environment 632, e.g., along an entire length of the central cavity of the testing system. Alternatively, in one or more embodiments, collecting data from the plurality of pressure sensors and visually monitoring the loss control material and/or other fluid may not necessarily occur across the entire length of the testing environment 632. For example, in one or more embodiments, collecting data from the plurality of pressure sensors and visually monitoring the loss control material and/or other fluid may occur over an area that is less than the entire length of the testing environment 632. In one or more embodiments, collecting data from the plurality of pressure sensors and visually monitoring the loss control material and/or other fluid may occur at the first end of the testing system, the second end of the testing system, or at one or more points therebetween.

In one or more embodiments, the method for testing a loss control material may include injecting or inserting various testing units or formation samples to simulate different downhole drilling environments as well as formation types. As will be discussed below, a plurality of spherical testing units 410, shown in FIGS. 4A and 4B, may be used to simulate a particular type of formation, e.g., a vugular formation. In one or more embodiments, the plurality of spherical testing units may be disposed between an outer surface of the first plate and an outer surface of the second plate. In one or more embodiments, the plurality of spherical testing units may be disposed within a central cavity of the testing system, e.g., within the testing environment. Those having ordinary skill in the art will appreciate that the plurality of spherical testing units may be made from any material and may not necessarily be uniform in size or shape. For example, in one or more embodiments, the plurality of spherical testing units may be formed from acrylic, plastic, polymer, metal, or any other material. Further, in one or more embodiments, the plurality of spherical testing units may not necessarily be spherical. For example, in one or more embodiments, the plurality of testing units may be elliptical, pyramidal, or any other shape, and may vary in shape and dimensions. In other words, in one or more embodiments, the plurality of testing units that may be injected or inserted into the testing environment to simulate different downhole drilling environments and formation types may not necessarily be homogeneous in size, shape, or material.

In one or more embodiments, the plurality of testing units that may be injected or inserted into the testing environment to simulate different downhole drilling environments and formation types may be granular units. Further, in one or more embodiments, the plurality of testing units may include formation samples to be inserted into the testing environment. For example, in one or more embodiments, the plurality of testing units may include formation samples such as sand and/or clay. In one or more embodiments, sand samples injected or inserted into the testing environment may be granular, and clay samples may be plate-like in shape. Further, those having ordinary skill in the art will appreciate that any combination of the above-described testing units and formation samples may be injected or inserted into the testing environment to simulate different downhole drilling environments and formation types. For example, in one or more embodiments, a mixture of clay, sand, and/or acrylic spherical testing units that vary in diameter may be injected or inserted into the testing environment with or without a fluid.

As such, in one or more embodiments, one or more fluids, as the first fluid, the second fluid, and/or the third fluid, which may include water and/or a drilling mud material, and a loss control material may be circulated through the circulation line and the interaction of these fluids with a formation may be evaluated with the testing system. As a fluid is pumped through inlet, the fluid (and loss control material) may be in fluid contact with the central cavity, and fluid may flow to the circulation outlet, but may also be free to flow into the central cavity of testing system.

As discussed above, testing materials according to embodiments disclosed herein may include, without limitation, loss control material, drilling mud material, and water. For example, in one or more embodiments, once a first loss control material is injected into the testing system, e.g., into the central cavity of the testing system, a second loss control material may be injected into the testing system before a drilling mud material is injected into the system. In one or more embodiments, the second loss control material may be injected into the testing system simultaneously with another testing material, such as drilling mud material or water. Alternatively, in one or more embodiments, a loss control material may be may be injected into the testing system simultaneously with another testing material, as described above, and, subsequently, another testing material, such as drilling mud material or water, may be injected alone, i.e., without a loss control material, into the testing system. Those having ordinary skill in the art will appreciate that, according to embodiments disclosed herein, any number of fluids, i.e., any number of loss control materials, drilling fluids, water, or any other fluid known in the art, may be injected at any time into the testing system either alone or in combination with other fluids.

According to one or more embodiments, a testing system may include a first plate having an inlet, an outlet, and a plurality of openings formed through a surface of the first plate, a second plate engaged with the first plate, and a plurality of pressure sensors engaged with the first plate through the plurality of openings formed in the first plate, in which the first plate and the second plate are configured such that a central cavity is formed between a portion of the first plate and the second plate. In one or more embodiments, the first plate may have the central cavity formed therein. In one or more embodiments, the testing system may include a pump coupled to the first plate, the pump configured to inject a fluid through the inlet of the first plate. Further, in one or more embodiments, the testing system may include an accumulator coupled to the first plate, the accumulator configured to collect a fluid through the outlet of the first plate.

In one or more embodiments, the first plate of the testing system may include a plurality of engagement openings formed therethrough, in which the plurality of engagement openings of the first plate are configured to receive at least one engagement member. Further, in one or more embodiments, the second plate of the testing system may include a plurality of engagement openings formed therethrough, in which the plurality of engagement openings of the second plate are configured to receive at least one engagement member. In one or more embodiments, the first plate may be engaged with the second plate by the at least one engagement member.

Further, in one or more embodiments, the testing system may include an intermediate plate. In one or more embodiments, the intermediate plate may have a hole formed therethrough and may also have a plurality of engagement openings formed therethrough. In one or more embodiments, the plurality of engagement openings of the intermediate plate may be configured to receive at least one engagement member. In one or more embodiments, the first plate may be engaged with the intermediate plate, which may be engaged with the second plate, by the at least one engagement member.

Furthermore, in one or more embodiments, the first plate may include a recessed portion formed around the plurality of engagement openings of the first plate. In one or more embodiments, the testing system may include a sealing member disposed about the recessed portion of the first plate. In one or more embodiments, the testing system may include a plurality of spherical testing units disposed within the central cavity of the testing system.

The method of testing a loss control material, according to embodiments disclosed herein, may allow a user to measure a distance into the testing environment, e.g., a distance into the central cavity of the testing system, that certain loss control materials travel, a fluid may displace during downhole use both visually and with a pressure profile that may be generated using data collected by the plurality of pressure sensors. Such testing by a user may allow a user to simulate a distance into a formation a fluid may displace during downhole use. Further, the method of testing a loss control material, according to embodiments disclosed herein, may allow a user to measure a distance into the testing environment that other fluids, such as drilling mud material, displace. As discussed above, this distance displaced or traveled by the testing materials may be evaluated both visually and with a pressure profile that may be generated using data collected by the plurality of pressure sensors.

The foregoing description of the embodiments has been provided for purposes of illustration and description. Although the preceding description has been described herein with reference to particular means, materials, and embodiments, it is not intended to be limited to the particulars disclosed herein; rather, it extends to all functionally equivalent structures, methods, and uses, such as are within the scope of the appended claims.

What is claimed is:

1. A method comprising:
   filling a testing environment in a testing system with a first fluid;
   injecting a loss control material in a second fluid into the testing environment from a first end of the testing system, thereby displacing the first fluid across the testing environment to a second end of the testing system; and
   monitoring a formation of a barrier created by the loss control material, the monitoring comprising:
   collecting data from a plurality of pressure sensors; and
   generating a pressure profile along a length of the testing environment using the collected data.

2. The method of claim 1, wherein the plurality of pressure sensors are distributed at least between the first end and the second end of the testing system.

3. The method of claim 1, wherein collecting data from the plurality of pressure sensors comprises measuring pressure at the first end of the testing system, the second end of the testing system, and at any point in between the first end and the second end of the testing system.

4. The method of claim 1, further comprising injecting a third fluid into the testing environment.

5. The method of claim 4, wherein injecting the third fluid into the testing environment is a stepped injection.

6. The method of claim 4, further comprising circulating each of the first fluid, the second fluid, and the third fluid through the testing system.

7. The method of claim 6, wherein circulating each of the first fluid, the second fluid, and the third fluid through the testing system comprises circulating each of the first fluid, the second fluid, and the third fluid through the testing system in a direction that is substantially orthogonal to a fluid flow path between the first end and the second of the testing system.

8. The method of claim 1, further comprising applying a vacuum to the testing system.

9. The method of claim 1, further comprising visually monitoring the loss control material in the second fluid while the loss control material in the second fluid is injected into the testing system.

10. The method of claim 1, further comprising visually monitoring the third fluid while the third fluid is injected into the testing system.

11. The method of claim 1, wherein the testing system simulates a formation.

12. A testing system comprising:
    a first plate having an inlet, an outlet, and a plurality of openings formed through a surface of the first plate;
    a second plate engaged with the first plate,
    wherein the first plate and the second plate are configured such that a central cavity is formed between a portion of the first plate and the second plate; and
    a plurality of pressure sensors engaged with the first plate through the plurality of openings formed in the first plate.

13. The system of claim 12, further comprising an intermediate plate disposed between the first plate and the second plate, the intermediate plate having a central opening formed therethrough, the central opening forming the central cavity.

14. The system of claim 12, the first plate having the central cavity formed therein.

15. The system of claim 12, further comprising a pump coupled to the first plate, the pump configured to inject a fluid through the inlet of the first plate.

16. The system of claim 12, wherein the first plate is engaged with the second plate by at least one engagement member.

17. The system of claim 12, the first plate comprising a recessed portion formed around a plurality of engagement openings of the first plate.

18. The system of claim 17, further comprising a sealing member disposed about the recessed portion of the first plate.

19. The system of claim 12, further comprising a plurality of spherical testing units disposed within the central cavity.

20. The system of claim 12, further comprising a circulation line coupled to the inlet of the first plate and a circulation outlet formed on the second plate.

21. The system of claim 20, further comprising a circulation pump coupled to the circulation line.

22. The system of claim 12, wherein the first plate is formed from a substantially transparent material.

23. A method comprising:
    injecting a fluid into a testing environment of a testing system at a first end of the testing system, the fluid comprising a loss control material; and
    visually monitoring a flow profile of the fluid along a length of the testing environment through an at least partially transparent first plate of the testing system.

* * * * *